United States Patent
Raju

(10) Patent No.: US 11,779,478 B2
(45) Date of Patent: Oct. 10, 2023

(54) VENOUS AND ARTERIAL APPLICATION OF AN INCREASED VOLUMETRIC FLOW STENT AND MATCHING BALLOON

(71) Applicant: Seshadri Raju, Jackson, MS (US)

(72) Inventor: Seshadri Raju, Jackson, MS (US)

( * ) Notice: Subject to any disclaimer, the term of this patent is extended or adjusted under 35 U.S.C. 154(b) by 0 days.

(21) Appl. No.: 17/444,558

(22) Filed: Aug. 5, 2021

(65) Prior Publication Data
US 2022/0233338 A1    Jul. 28, 2022

Related U.S. Application Data

(63) Continuation-in-part of application No. PCT/US2020/016895, filed on Feb. 5, 2020.

(60) Provisional application No. 62/801,912, filed on Feb. 6, 2019.

(51) Int. Cl.
| | |
|---|---|
| *A61F 2/82* | (2013.01) |
| *A61F 2/852* | (2013.01) |
| *A61F 2/844* | (2013.01) |
| *A61F 2/90* | (2013.01) |
| *A61F 2/958* | (2013.01) |

(52) U.S. Cl.
CPC .............. *A61F 2/852* (2013.01); *A61F 2/844* (2013.01); *A61F 2/90* (2013.01); *A61F 2/958* (2013.01); *A61F 2002/826* (2013.01); *A61F 2002/9583* (2013.01); *A61F 2250/0039* (2013.01)

(58) Field of Classification Search
CPC .... A61F 2/82; A61F 2/90; A61F 2/852; A61F 2002/826
See application file for complete search history.

(56) References Cited

U.S. PATENT DOCUMENTS

| | | |
|---|---|---|
| 5,935,108 A | 8/1999 | Katoh et al. |
| 6,582,472 B2 | 6/2003 | Hart |
| 9,764,067 B2 | 9/2017 | Fleury et al. |
| 10,064,745 B2 | 9/2018 | Hossainy et al. |
| 2003/0135266 A1* | 7/2003 | Chew ........................ A61F 2/91 623/1.16 |

(Continued)

OTHER PUBLICATIONS

PCT/US2020/016895—see the Written Opinion of the International Sarching Authority (dated May 7, 2020), International Search Report (dated May 7, 2020), and International Preliminary Report on Patentability (dated Jul. 20, 2021).

*Primary Examiner* — William H Matthews
(74) *Attorney, Agent, or Firm* — Intellectual Property Consulting, LLC; Bernard F. Meroney

(57) ABSTRACT

The invention includes an expandable stent having a tubular shape when expanded, the shape including a portion t where the stent radius grows with stent length so that the growth in the portion is constant conductance growth or near-constant conductance growth. The invention includes sheaths that will encase the stent to restrict the growth of the stent to the desired expanded shape. The invention also includes expandable stent balloons that expand the stent to the desired shape configuration with constant or near constant conductance portion. The balloons can include a similar sheath or sleeve to restrict the balloon's growth to the desired shape. The stent radius growth can be piecewise, and is not necessarily $4^{th}$ order growth, but can be such that $r^n/l$ is a constant in the portion, where n>4.

13 Claims, 26 Drawing Sheets

(56) References Cited

U.S. PATENT DOCUMENTS

2007/0106365 A1\* 5/2007 Andreas .................. A61F 2/958
623/1.11

\* cited by examiner

Fig. 3A
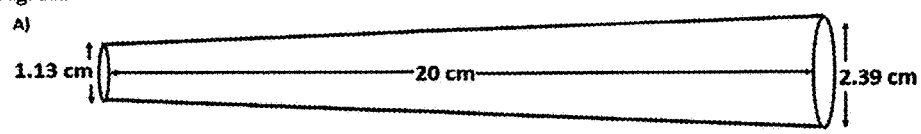
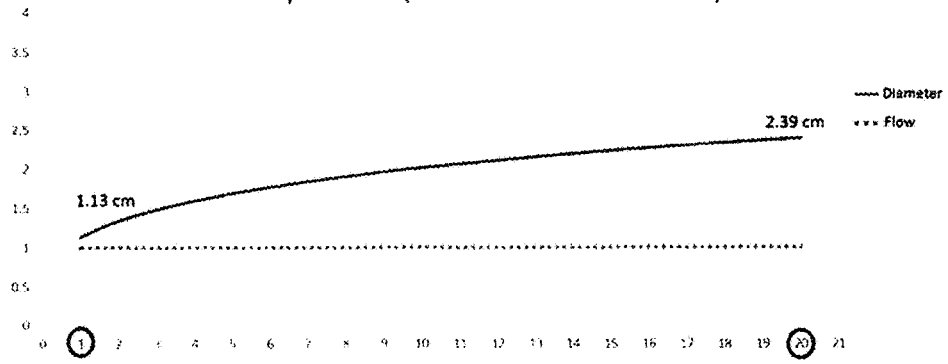
Fig 3B

Fig. 4A-1.
Fig. 4A-2.
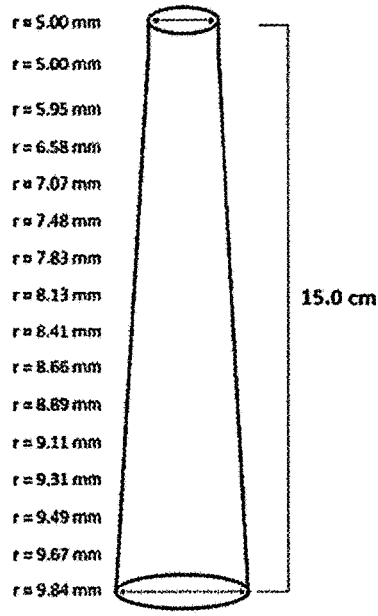
CONSTANT CONDUCTANCE STENT
Initial diameter = 10 mm
Constant Conductance = 0.614
FIG 4A-1

CONSTANT CONDUCTANCE STENT

Initial diameter = 12 mm
Constant Conductance = 1.272

Fig. 5A

Starting Diameter = 1 cm

| Length (cm) | Radius (cm) | Diameter (cm) | Geometric Factor ($R_{cm}^4/L_{cm}$) |
|---|---|---|---|
| 1 | 0.5000 | 1.0000 | 0.0625 |
| 2 | 0.5946 | 1.1892 | 0.0625 |
| 3 | 0.6580 | 1.3161 | 0.0625 |
| 4 | 0.7071 | 1.4142 | 0.0625 |
| 5 | 0.7477 | 1.4953 | 0.0625 |
| 6 | 0.7825 | 1.5651 | 0.0625 |
| 7 | 0.8133 | 1.6266 | 0.0625 |
| 8 | 0.8409 | 1.6818 | 0.0625 |
| 9 | 0.8660 | 1.7321 | 0.0625 |
| 10 | 0.8891 | 1.7783 | 0.0625 |
| 11 | 0.9106 | 1.8212 | 0.0625 |
| 12 | 0.9306 | 1.8612 | 0.0625 |
| 13 | 0.9494 | 1.8988 | 0.0625 |
| 14 | 0.9672 | 1.9343 | 0.0625 |
| 15 | 0.9840 | 1.9680 | 0.0625 |
| 16 | 1.0000 | 2.0000 | 0.0625 |

Fig. 5B

Starting Diameter = 1.2 cm

| Length (cm) | Radius (cm) | Diameter (cm) | Geometric Factor ($R_{cm}^4/L_{cm}$) |
|---|---|---|---|
| 1 | 0.6000 | 1.2000 | 0.1296 |
| 2 | 0.7135 | 1.4270 | 0.1296 |
| 3 | 0.7896 | 1.5793 | 0.1296 |
| 4 | 0.8485 | 1.6971 | 0.1296 |
| 5 | 0.8972 | 1.7944 | 0.1296 |
| 6 | 0.9391 | 1.8781 | 0.1296 |
| 7 | 0.9759 | 1.9519 | 0.1296 |
| 8 | 1.0091 | 2.0182 | 0.1296 |
| 9 | 1.0392 | 2.0785 | 0.1296 |
| 10 | 1.0670 | 2.1339 | 0.1296 |
| 11 | 1.0927 | 2.1854 | 0.1296 |
| 12 | 1.1167 | 2.2335 | 0.1296 |
| 13 | 1.1393 | 2.2786 | 0.1296 |
| 14 | 1.1606 | 2.3212 | 0.1296 |
| 15 | 1.1808 | 2.3616 | 0.1296 |
| 16 | 1.2000 | 2.4000 | 0.1296 |

Fig. 6A-1

| Length (cm) | Radius (mm) | Diameter (mm) | Geometric Factor ($r_{cm}^4/L_{cm}$) |
|---|---|---|---|
| 1 | 0.5000 | 1.0000 | 0.00000625 |
| 2 | 0.5946 | 1.1892 | 0.00000625 |
| 3 | 0.6580 | 1.3161 | 0.00000625 |
| 4 | 0.7071 | 1.4142 | 0.00000625 |
| 5 | 0.7477 | 1.4953 | 0.00000625 |
| 6 | 0.7825 | 1.5651 | 0.00000625 |
| 7 | 0.8133 | 1.6266 | 0.00000625 |
| 8 | 0.8409 | 1.6818 | 0.00000625 |
| 9 | 0.8660 | 1.7321 | 0.00000625 |
| 10 | 0.8891 | 1.7783 | 0.00000625 |
| 11 | 0.9106 | 1.8212 | 0.00000625 |
| 12 | 0.9306 | 1.8612 | 0.00000625 |
| 13 | 0.9494 | 1.8988 | 0.00000625 |
| 14 | 0.9672 | 1.9343 | 0.00000625 |
| 15 | 0.9840 | 1.9680 | 0.00000625 |
| 16 | 1.0000 | 2.0000 | 0.00000625 |
| 17 | 1.0153 | 2.0305 | 0.00000625 |
| 18 | 1.0299 | 2.0598 | 0.00000625 |
| 19 | 1.0439 | 2.0878 | 0.00000625 |
| 20 | 1.0574 | 2.1147 | 0.00000625 |
| 21 | 1.0703 | 2.1407 | 0.00000625 |
| 22 | 1.0829 | 2.1657 | 0.00000625 |
| 23 | 1.0950 | 2.1899 | 0.00000625 |
| 24 | 1.1067 | 2.2134 | 0.00000625 |
| 25 | 1.1180 | 2.2361 | 0.00000625 |
| 26 | 1.1291 | 2.2581 | 0.00000625 |
| 27 | 1.1398 | 2.2795 | 0.00000625 |
| 28 | 1.1502 | 2.3003 | 0.00000625 |
| 29 | 1.1603 | 2.3206 | 0.00000625 |
| 30 | 1.1702 | 2.3403 | 0.00000625 |

Fig. 6A-2

| Length (cm) | Radius (mm) | Diameter (mm) | Geometric Factor ($r_{cm}^4/L_{cm}$) |
|---|---|---|---|
| 1 | 1.0000 | 2.0000 | 0.0001 |
| 2 | 1.1892 | 2.3784 | 0.0001 |
| 3 | 1.3161 | 2.6321 | 0.0001 |
| 4 | 1.4142 | 2.8284 | 0.0001 |
| 5 | 1.4953 | 2.9907 | 0.0001 |
| 6 | 1.5651 | 3.1302 | 0.0001 |
| 7 | 1.6266 | 3.2532 | 0.0001 |
| 8 | 1.6818 | 3.3636 | 0.0001 |
| 9 | 1.7321 | 3.4641 | 0.0001 |
| 10 | 1.7783 | 3.5566 | 0.0001 |
| 11 | 1.8212 | 3.6423 | 0.0001 |
| 12 | 1.8612 | 3.7224 | 0.0001 |
| 13 | 1.8988 | 3.7977 | 0.0001 |
| 14 | 1.9343 | 3.8687 | 0.0001 |
| 15 | 1.9680 | 3.9360 | 0.0001 |
| 16 | 2.0000 | 4.0000 | 0.0001 |
| 17 | 2.0305 | 4.0611 | 0.0001 |
| 18 | 2.0598 | 4.1195 | 0.0001 |
| 19 | 2.0878 | 4.1756 | 0.0001 |
| 20 | 2.1147 | 4.2295 | 0.0001 |
| 21 | 2.1407 | 4.2814 | 0.0001 |
| 22 | 2.1657 | 4.3315 | 0.0001 |
| 23 | 2.1899 | 4.3799 | 0.0001 |
| 24 | 2.2134 | 4.4267 | 0.0001 |
| 25 | 2.2361 | 4.4721 | 0.0001 |
| 26 | 2.2581 | 4.5162 | 0.0001 |
| 27 | 2.2795 | 4.5590 | 0.0001 |
| 28 | 2.3003 | 4.6007 | 0.0001 |
| 29 | 2.3206 | 4.6412 | 0.0001 |
| 30 | 2.3403 | 4.6807 | 0.0001 |

Fig. 6A-3.

| Length (cm) | Radius (mm) | Diameter (mm) | Geometric Factor ($r_{cm}^4/L_{cm}$) |
|---|---|---|---|
| 1 | 2.0000 | 4.0000 | 0.0016 |
| 2 | 2.3784 | 4.7568 | 0.0016 |
| 3 | 2.6321 | 5.2643 | 0.0016 |
| 4 | 2.8284 | 5.6569 | 0.0016 |
| 5 | 2.9907 | 5.9814 | 0.0016 |
| 6 | 3.1302 | 6.2603 | 0.0016 |
| 7 | 3.2532 | 6.5063 | 0.0016 |
| 8 | 3.3636 | 6.7272 | 0.0016 |
| 9 | 3.4641 | 6.9282 | 0.0016 |
| 10 | 3.5566 | 7.1131 | 0.0016 |
| 11 | 3.6423 | 7.2846 | 0.0016 |
| 12 | 3.7224 | 7.4448 | 0.0016 |
| 13 | 3.7977 | 7.5953 | 0.0016 |
| 14 | 3.8687 | 7.7373 | 0.0016 |
| 15 | 3.9360 | 7.8720 | 0.0016 |
| 16 | 4.0000 | 8.0000 | 0.0016 |
| 17 | 4.0611 | 8.1222 | 0.0016 |
| 18 | 4.1195 | 8.2391 | 0.0016 |
| 19 | 4.1756 | 8.3512 | 0.0016 |
| 20 | 4.2295 | 8.4590 | 0.0016 |
| 21 | 4.2814 | 8.5628 | 0.0016 |
| 22 | 4.3315 | 8.6629 | 0.0016 |
| 23 | 4.3799 | 8.7598 | 0.0016 |
| 24 | 4.4267 | 8.8535 | 0.0016 |
| 25 | 4.4721 | 8.9443 | 0.0016 |
| 26 | 4.5162 | 9.0324 | 0.0016 |
| 27 | 4.5590 | 9.1180 | 0.0016 |
| 28 | 4.6007 | 9.2013 | 0.0016 |
| 29 | 4.6412 | 9.2824 | 0.0016 |
| 30 | 4.6807 | 9.3614 | 0.0016 |

Fig. 6A-4.

| Length (cm) | Radius (mm) | Diameter (mm) | Geometric Factor ($r_{cm}^4/L_{cm}$) |
|---|---|---|---|
| 1 | 4.0000 | 8.0000 | 0.0256 |
| 2 | 4.7568 | 9.5137 | 0.0256 |
| 3 | 5.2643 | 10.5286 | 0.0256 |
| 4 | 5.6569 | 11.3137 | 0.0256 |
| 5 | 5.9814 | 11.9628 | 0.0256 |
| 6 | 6.2603 | 12.5207 | 0.0256 |
| 7 | 6.5063 | 13.0126 | 0.0256 |
| 8 | 6.7272 | 13.4543 | 0.0256 |
| 9 | 6.9282 | 13.8564 | 0.0256 |
| 10 | 7.1131 | 14.2262 | 0.0256 |
| 11 | 7.2846 | 14.5693 | 0.0256 |
| 12 | 7.4448 | 14.8897 | 0.0256 |
| 13 | 7.5953 | 15.1906 | 0.0256 |
| 14 | 7.7373 | 15.4747 | 0.0256 |
| 15 | 7.8720 | 15.7439 | 0.0256 |
| 16 | 8.0000 | 16.0000 | 0.0256 |
| 17 | 8.1222 | 16.2443 | 0.0256 |
| 18 | 8.2391 | 16.4781 | 0.0256 |
| 19 | 8.3512 | 16.7024 | 0.0256 |
| 20 | 8.4590 | 16.9179 | 0.0256 |
| 21 | 8.5628 | 17.1256 | 0.0256 |
| 22 | 8.6629 | 17.3259 | 0.0256 |
| 23 | 8.7598 | 17.5195 | 0.0256 |
| 24 | 8.8535 | 17.7069 | 0.0256 |
| 25 | 8.9443 | 17.8885 | 0.0256 |
| 26 | 9.0324 | 18.0648 | 0.0256 |
| 27 | 9.1180 | 18.2361 | 0.0256 |
| 28 | 9.2013 | 18.4026 | 0.0256 |
| 29 | 9.2824 | 18.5648 | 0.0256 |
| 30 | 9.3614 | 18.7228 | 0.0256 |

Fig. 6A-5

| Length (cm) | Radius (mm) | Diameter (mm) | Geometric Factor ($r_{cm}^4/L_{cm}$) |
|---|---|---|---|
| 1 | 16.0000 | 32.0000 | 6.5536 |
| 2 | 19.0273 | 38.0546 | 6.5536 |
| 3 | 21.0572 | 42.1144 | 6.5536 |
| 4 | 22.6274 | 45.2548 | 6.5536 |
| 5 | 23.9256 | 47.8512 | 6.5536 |
| 6 | 25.0414 | 50.0827 | 6.5536 |
| 7 | 26.0252 | 52.0504 | 6.5536 |
| 8 | 26.9087 | 53.8174 | 6.5536 |
| 9 | 27.7128 | 55.4256 | 6.5536 |
| 10 | 28.4525 | 56.9049 | 6.5536 |
| 11 | 29.1386 | 58.2771 | 6.5536 |
| 12 | 29.7794 | 59.5587 | 6.5536 |
| 13 | 30.3813 | 60.7625 | 6.5536 |
| 14 | 30.9494 | 61.8988 | 6.5536 |
| 15 | 31.4878 | 62.9757 | 6.5536 |
| 16 | 32.0000 | 64.0000 | 6.5536 |
| 17 | 32.4887 | 64.9774 | 6.5536 |
| 18 | 32.9563 | 65.9125 | 6.5536 |
| 19 | 33.4048 | 66.8095 | 6.5536 |
| 20 | 33.8359 | 67.6718 | 6.5536 |
| 21 | 34.2511 | 68.5022 | 6.5536 |
| 22 | 34.6518 | 69.3036 | 6.5536 |
| 23 | 35.0390 | 70.0780 | 6.5536 |
| 24 | 35.4138 | 70.8276 | 6.5536 |
| 25 | 35.7771 | 71.5542 | 6.5536 |
| 26 | 36.1296 | 72.2592 | 6.5536 |
| 27 | 36.4721 | 72.9442 | 6.5536 |
| 28 | 36.8052 | 73.6105 | 6.5536 |
| 29 | 37.1295 | 74.2591 | 6.5536 |
| 30 | 37.4456 | 74.8911 | 6.5536 |

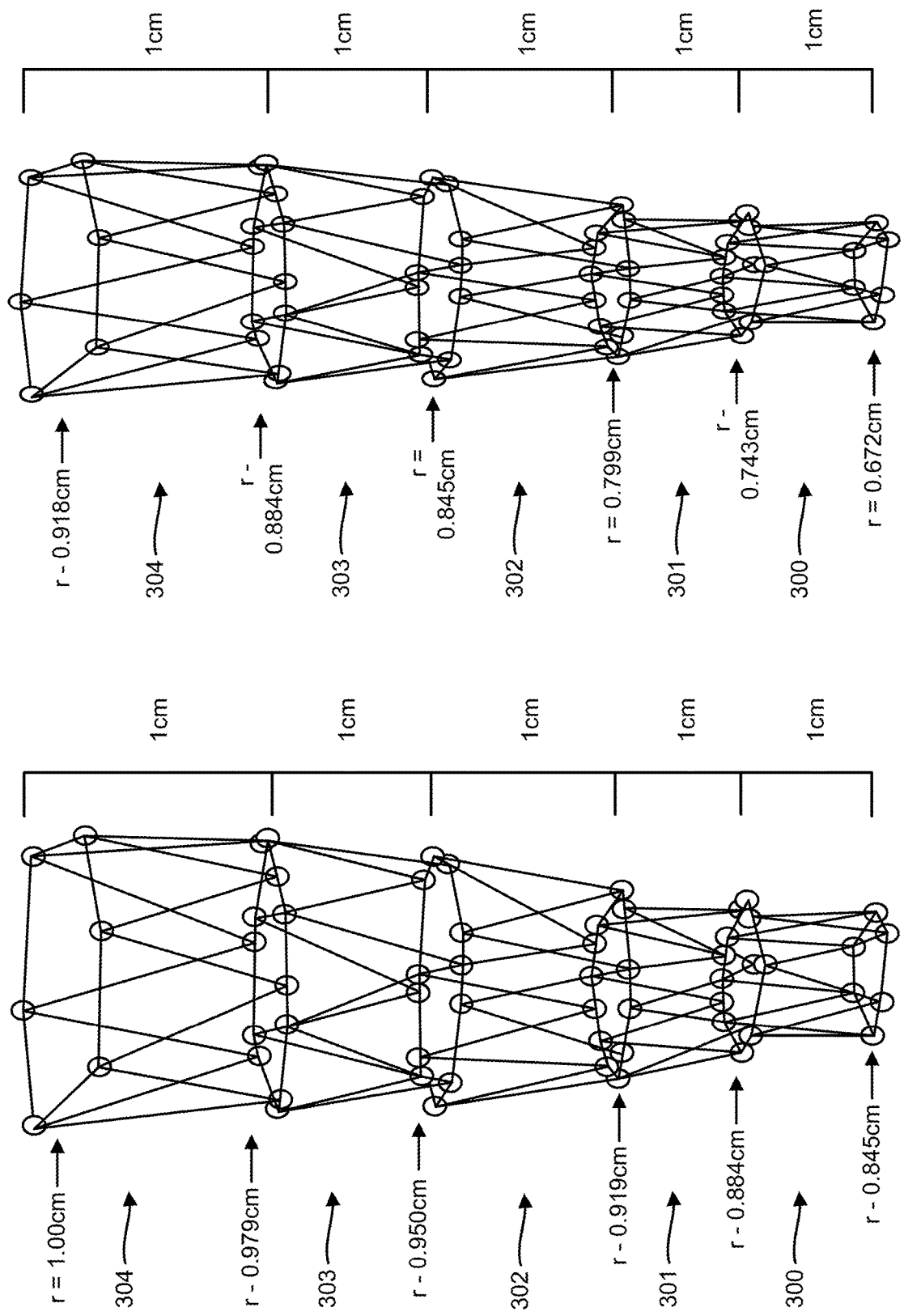

VENOUS AND ARTERIAL APPLICATION OF AN INCREASED VOLUMETRIC FLOW STENT AND MATCHING BALLOON

PRIORITY CLAIM

This application is a continuation in part of PCT/US20/16895 filed on May 2, 2020. which claimed the priority benefit of U.S. Provisional Patent 62/801,912 filed on Feb. 6, 2019, which is incorporated by reference in its entirety.

BACKGROUND OF THE INVENTION

Stenosis is a narrowing or partial occlusion of a lumen, such as in the arterial or venous system. A focal stenosis is characterized by a rapid change in lumen cross-sectional area that occurs over a very short segment length of the vessel, typically over a length of about 1 to 2 cm. Diffuse stenosis is stenosis that is not focal and is characterized by a narrowing of the lumen which occurs over greater vessel segment length, typically lengths greater than 2 cm. Stenosis is accompanied by changes in velocity of blood flow through the narrowed lumen.

A stenosis is often treated with a stent. Stents are generally cylindrically shaped devices which function to expand when deployed. Stents may be balloon expandable or self-expanding. The balloon expandable stent is a stent that is usually made of a coil, mesh, or zigzag design. The stent is pre-mounted on a balloon and the inflation of the balloon plastically expands the stent with respect to the balloon diameter. Self-expanding stents are tubular devices stored in an elongated configuration in what is called a delivery system or applicator. The applicator is introduced percutaneously into the body into a vessel at a suitable location and guided through the vessel lumen to the location where the stent is to be released. The delivery system and the stent are often provided with radiological markers with which the positioning and the release of the stent can be monitored in situ under fluoroscopy. Upon release, the stent material auto expands to a predetermined size. Auto expansion is rather weak in many self-expanding stents. This may require pre-dilatation of the stenotic lesion with a balloon of appropriate size before the stent is deployed to enable it to expand to its intended size. In some stents, auto expansion must be assisted with 'post-dilatation' for full expansion of the stent to occur.

Commonly used self-expanding stents are braided stents, or laser cut stents. A braided stent is a metal stent that is produced by what is called a plain weaving technique. It is composed of a hollow body, which can stretch in the longitudinal direction and whose jacket is a braid made up of a multiplicity of filament-like elements which, in the expanded state of the braided stent, intersects a plane perpendicular to the longitudinal direction at a braid angle. Laser cut stents are constructed from a tube of material (most frequently, nitinol, a nickel titanium alloy), and stainless steel, cobalt, etc. that is laser-cut during production to create a meshed device. The tube is comprised of sequential aligned annular rings that are interconnected in a helical fashion. The tube is compressed and loaded into the delivery device and expands to original size when released. Nitinol, which has thermal memory, may help stents made of this material expand into position when exposed to body temperature after delivery. Compared with self-expanding braided stents, laser cut stents provide more accurate stent deployment with less foreshortening. Laser cut stents are much less subject to foreshortening but are probably less rigid than braided stents.

The stent, after expansion, is intended to restore the occluded vessel to normal or near normal flow conditions in the stented area. In the arterial and venous system, the stented area should have smooth laminar blood flow of uniform velocity. To help avoid restenosis, or the depositing of material in the stented vein, and the resultant re-occurrence of an occlusion, maintaining adequate flow through the stent is desirable. Unfortunately, existing stents do not provide such. A better stent product is needed.

SUMMARY OF THE INVENTION

A stent that contains a portion of the stent that has increased flow or "unitary," or constant conductance flow, where the radius r of the portion expands with the length l so that so that $r^4/l$ remains constant in the portion, or near constant conductance flow, where the radius expands with the length of the portion of the stent so that $r^n/l$, remains constant, where n>4, in the near constant conductance portion.

BRIEF DESCRIPTION OF THE DRAWINGS

FIG. 3A shows one embodiment of the invention with a 20 cm length and a starting diameter of 1.13 cm.

FIG. 3B is a graph of diameter versus flow through the unitary stent of FIG. 3A.

FIG. 4A-1 is a side perspective view of a constant conductance flow stent of length 16.0 cm with initial diameter of 10 mm, indicating the radius of the stent at 1 cm intervals along the stent.

FIG. 4A-2 is a side perspective view of a constant conductance flow stent of length 15.0 cm with initial diameter of 10 mm, indicating the radius of the stent at 1 cm intervals along the stent.

FIG. 4B-1 is a side perspective view of a constant conductance flow stent of length 16.0 cm with initial diameter of 12 mm, indicating the radius of the stent at 1 cm intervals along the stent.

FIG. 4B-2 is a side perspective view of a constant conductance flow stent of length 15.0 cm with initial diameter of 12 mm, indicating the radius of the stent at 1 cm intervals along the stent.

FIG. 5A is table for a constant conductance flow stent of starting diameter 1 cm, showing the change of radius with length L of the stent and showing the constant geometric factor of $R^4/L$ along the length L of the stent.

FIG. 5B is table for a constant conductance flow stent of starting diameter 1.2 cm, showing the change of radius with length L of the stent and showing the constant geometric factor of $R^4/L$ along the length L of the stent.

FIG. 6A-1 is an Excel spread sheet for a constant conductance flow stent of initial radius 0.5 mm (diameter of 1 mm) depicting the variation in radius and diameter in 1 cm intervals and showing the constant geometric factor.

FIG. 6A-2 is an Excel spread sheet for a constant conductance flow stent of initial radius of 1 mm (diameter of 2 mm) depicting the variation in radius and diameter in 1 cm intervals and showing the constant geometric factor.

FIG. 6A-3 is an Excel spread sheet for a constant conductance flow stent of initial radius of 2 mm (diameter of 4 mm) depicting the variation in radius and diameter in 1 cm intervals and showing the constant geometric factor.

FIG. 6A-4 is an Excel spread sheet for a constant conductance flow stent of initial radius of 4 mm (diameter of 8 mm) depicting the variation in radius and diameter in 1 cm intervals and showing the constant geometric factor.

FIG. 6A-5 is an Excel spread sheet for a constant conductance flow stent of initial radius of 16 mm (diameter of 32 mm) depicting the variation in radius and diameter in 1 cm intervals and showing the constant geometric factor.

FIG. 7C-1 shows a side perspective view of an 8 cm long constant conductance flow stent of initial diameter of 10 mm.

FIG. 7C-2 shows a side perspective view of a 7 cm long constant conductance flow stent of initial diameter of 32 mm.

FIG. 7D-1 shows a perspective view of a constant conductance flow balloon that has a portion matching the characteristics of the stent of FIG. 7C-1.

FIG. 7D-2 shows a perspective view of a constant conductance flow balloon that has a portion matching the characteristics of the stent of FIG. 7C-2.

FIG. 12-1 shows a perspective view of a near constant conductance flow segmented stent built using five Z stents. Each Z stent segment is 1 cm long. The initial and ending diameter of each segment are a diameter that would be appropriate for a constant conductance flow stent over that 1 cm segment, where the radius of the initial segment is 0.845 cm. The growth of each Z stent segment is not necessarily "constant conductance," but can be linear as is shown.

FIG. 12-2 shows a constant flow-like segmented stent built using five Z stents. Each Z stent segment is 1 cm long. The initial and ending diameter of each segment are a diameter that would be appropriate for a constant conductance flow stent over that 1 cm segment, where the radius of the initial segment is 0.672 cm.

FIG. 12-3 shows a near constant conductance like segmented stent built using five Z stents. Each Z stent segment is 1 cm long. The initial and ending diameter of each segment are a diameter that would be appropriate for a constant conductance flow stent over that 1 cm segment, where the radius of the initial segment is 0.351 cm.

DETAILED DESCRIPTION OF PREFERRED EMBODIMENTS OF THE INVENTION

Figure 1:
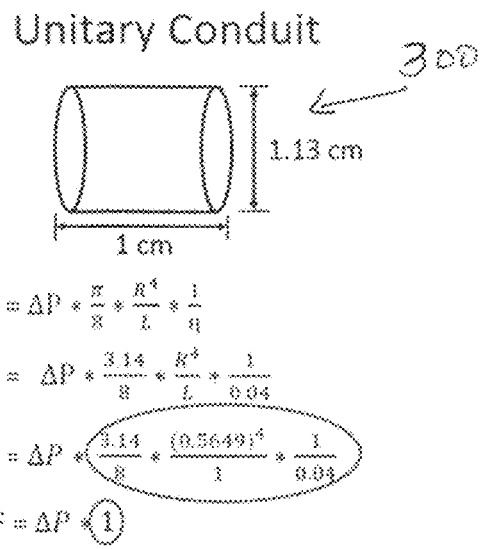
FIG. 1 is a side perspective view of an embodiment of a 1 cm unitary stent with the relevant flow equations showing flow through this embodiment.

Venous system blood flow is normally modeled with Poiseuille law, and hydrodynamic relationships, including the expression between flow, pressure, and resistance. The unitary conduit, or increased flow conduit, or constant conductance flow conduit concept described here and in FIG. 1 is particularly important in venous flow where pressure heads are very low. In certain arterial stenosis that are multiple or diffuse, the unitary conduit principles may be important as well. In small conduits such as coronaries, and small veins, thrombosis of the stent is a risk if flow falls below a certain critical level. The unitary or constant conductance flow conduit may perform better under these conditions. The relevant flow equations are as follows:

Poiseuille equation, Volumetric Fluid flow, $Q=\Delta P/R$ where $1/R$ is known as the conductance and where $R=8\mu L/\pi r^4$ and where $\mu$ is the fluid viscosity Rearranging, and combining the two equations:

$$Q=\Delta P*(\pi/8)*(r^4/L)*(1/\mu).$$

where L represents the length of the cylinder (stent) (measured from the start of the stent), the last three terms represent the numeric, geometric or growth and viscosity factors respectively. Q, or volumetric fluid flow (m³/sec) or flow, in the venous system, is generally measured in ml/sec or liters/min. In low pressure areas of the arterial system, these relationships can also be used for modeling flow. For instance, we constructed a "unitary" conduit with an initial diameter of 11.2 mm with an initial section of 1 cm of constant radius and expanding to an end diameter of 17.7 mm at a length of 6 cm. The radius expanded with length l so that $r^4/l=(0.56)^4$. We compared fluid flow through the unitary conduit to a second uniform diameter or non-unitary conduit. A total of 4.5 liters was run through each conduit with a head pressure of 25 mm Hg. The time taken to empty the 4.5 l from the reservoir is shown in Table 1 below.

TABLE 1

| Trial | Non-Unitary Uniform Conduit Time (seconds) | Trial | Unitary Conduit Time (seconds) |
| --- | --- | --- | --- |
| 1 | 64 | 1 | 43 |
| 2 | 64 | 2 | 41 |
| 3 | 66 | 3 | 44 |
| 4 | 68 | 4 | 45 |
| 5 | 68 | 5 | 45 |
| Average Time | 66 | Average Time | 43.6 |
| Average Flowrate | 68 mL/sec | Average Flowrate | 103 mL/sec |

Thus, the flow rate for the increased flow or unitary conduit was 103 mL/sec and was 68 mL/sec (averaged) for the non-unitary or uniform conduit (constant diameter). As can be seen, errors in the stent radius can have significant consequences on blood flow.

Figure 2:
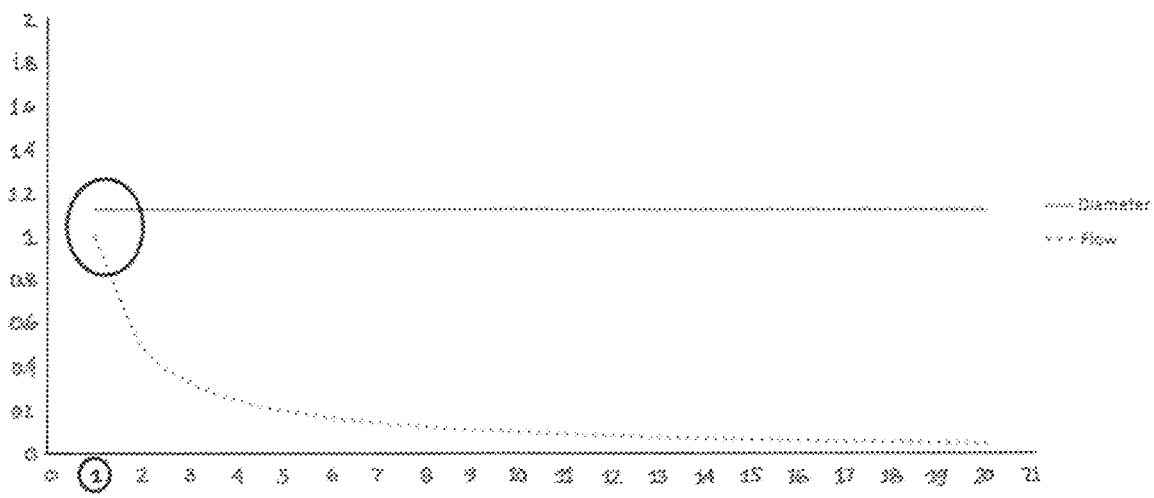
FIG. 2 is a graph showing decline in flow with length through conduits of uniform diameter
Figures 3, 12:
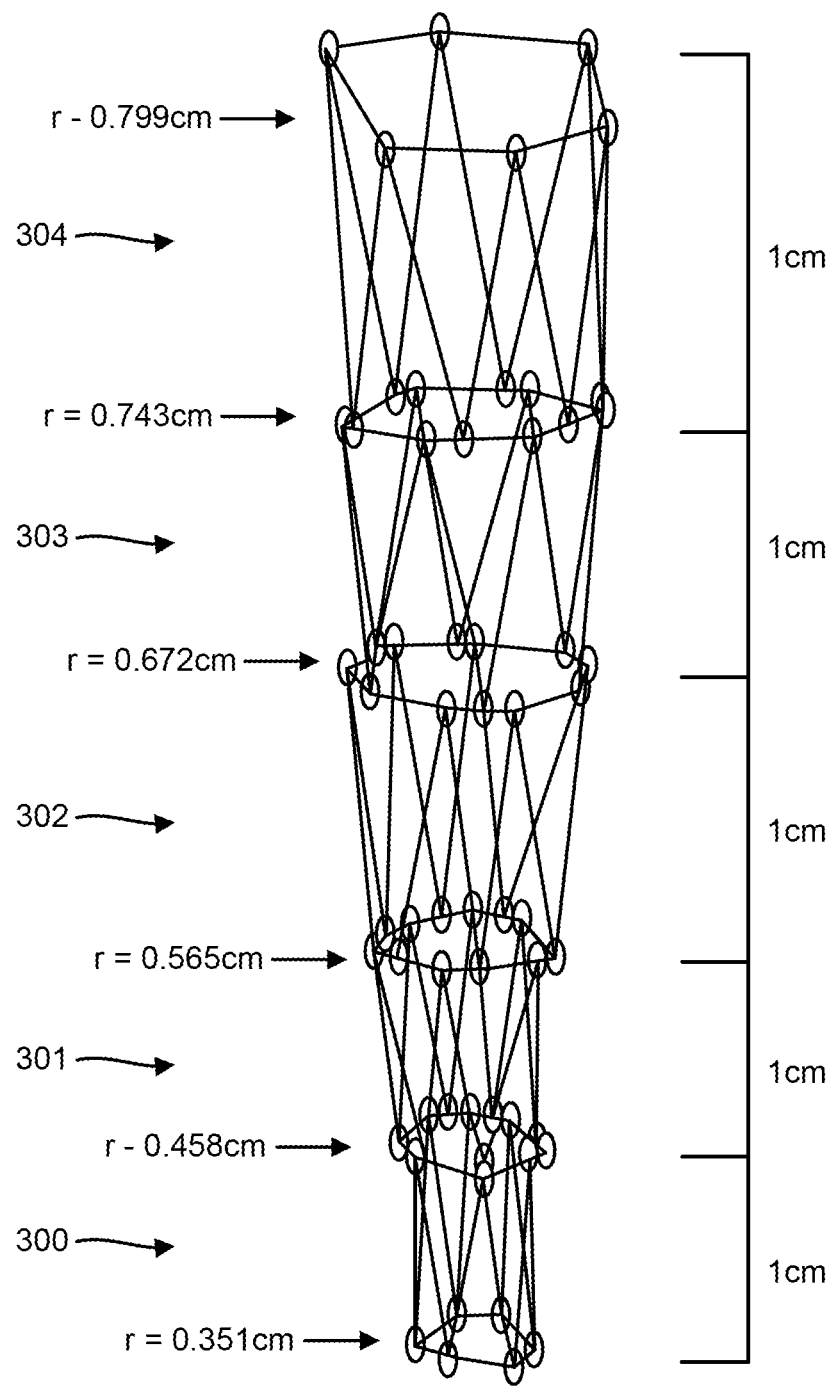

The flow equations can be simplified further by inserting known values for $\pi$ and $\mu$ (the viscosity of blood). As shown in FIG. 1, for a unitary conduit 300 of 1 cm in length with a diameter of 11.3 mm, the formula further reduces to: $Q=\Delta P*1=\Delta P$. Such a "unitary conduit'" will have a constant conductance of exactly 1, allowing flow to be directly proportional to the pressure head. However, if the conduit is extended beyond 1 cm, (with constant radius), the flow will decline, as increasing length in the denominator will reduce conductance and flow will be reduced under a constant pressure head (see FIG. 2). This reduction in flow can be partially compensated for by increasing the radius slightly with the length (that is, r is a function of L and is not constant), to maintain a constant geometric factor $r^4/L$, and hence, constant conductance. In the constant conductance section, the flow is directly proportional to the pressure head $\Delta P$. A relatively small increase in radius with length is needed as conduit radius (r) enters the equation in the fourth power in the numerator, while the length (L) is the denominator in the first power. See FIG. 3A. A conduit or stent that expands the radius with length so that $r^4/L$ remains constant is called a "unitary" or constant conductance flow stent, herein, having increased flow characteristics. As shown in FIG. 3B, the flow in a constant conductance stent is almost constant. For this reason, a constant conductance stent may be referred to as a constant flow stent herein. The concept is to keep the conductance or flow constant in the stent, which can be achieved by maintaining the geometric factor $(r^4/L)$ a constant value K in the stent. In these instances, the radius grows with the length of the stent, and as used herein R4 growth means $r=K*(\sqrt[4]{L})$, or $(r^4/L=k$, where K is a constant. All examples used herein will have the stent grow after the first 1 cm of length, where the first cm preferably has a constant radius, thus avoiding the ambiguity of examining $r^4/L$ as $L \rightarrow 0$.

In reality, a graft or stent starts in an existing conduit. That implies that the initial conduit combination can be viewed as a single conduit. To determine the "effective length" of that portion of the conduit before the onset of the graft or stent, we have $L=(\Delta P r^4 * \pi)/(Q*8*\mu)=L_{EFF}$, the effective length). Consequently, the combined "conduit" at the beginning of the stent or graft has a length, and the length of the "stent" or graft will never be zero. Use of a 1 cm starting length is arbitrary, but not unreasonable, the measured Q (such as estimated from doppler sonar), and $\Delta P$, within biological systems other than arterial, should be small, so L will not be very large. Hence, using a 1 cm constant diameter starting stent is not unreasonable, as it unlikely changes L significantly. Alternatively, the diameter for a specific length to start R4 growth can be chosen, as well as the stent starting diameter for R4 growth after the specific length; then providing for a smooth transition from the starting radius to the radius at the start of R4 growth (such as a linear transition) can be selected The preferred constant value will be $ri^4/(L)$ where ri is the starting radius of the unitary section near the beginning of the stent. L, as described above or as used in the examples herein, is set as 1 cm, the actual stent length at the start of the growth section in the examples. If the expanding portion or as used herein, is set as 1 cm. If the expanding portion of the stent starts at length LSO, with radius ri at this length, the constant K will be $ri^4/(LSO)$. If the expansion section starts at the beginning of the stent (here measured length=0), then LSO is a value greater than zero, preferably ($L_{eff}$) If the growth section is near the beginning of the stent, then the preferred constant value will be $ri^4/(L_{eff}+LSO)$ where $L_{eff}$ is described above, and LSO is the actual length of the stent at the start of the growth.

Figures 1, 4B:
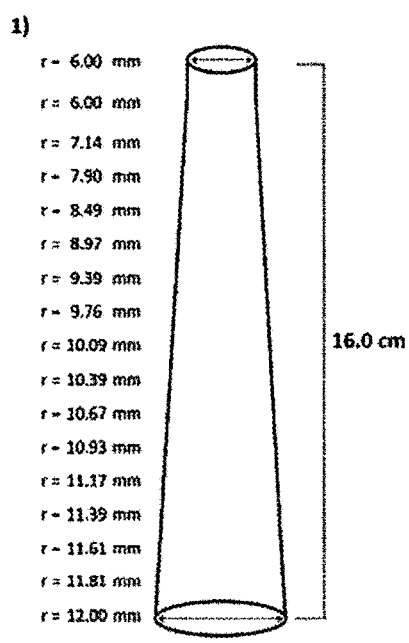
Figures 2, 4B:
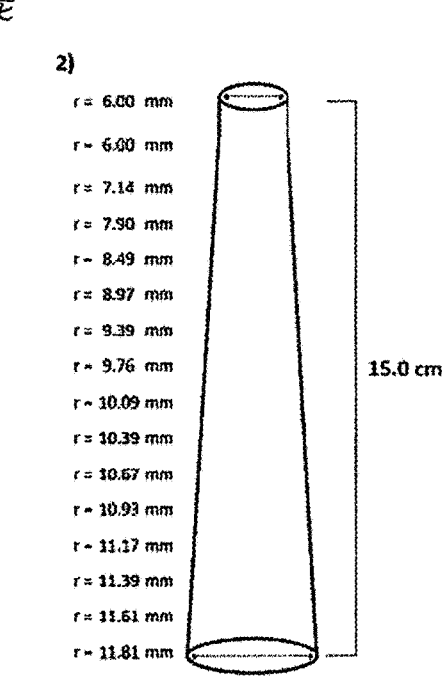
Figure 7A:
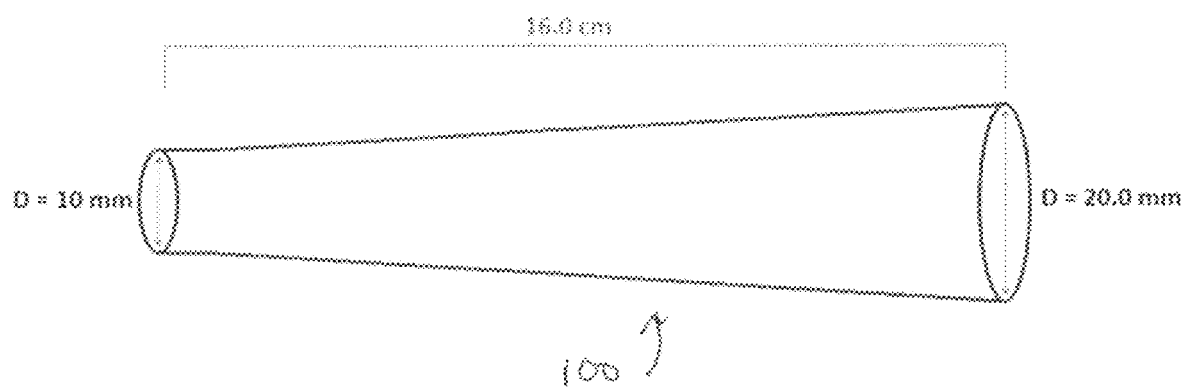
FIG. 7A is a side perspective view of a constant conductance flow stent with initial diameter of 10 mm, with a length of 16 cm.
Figure 7B:
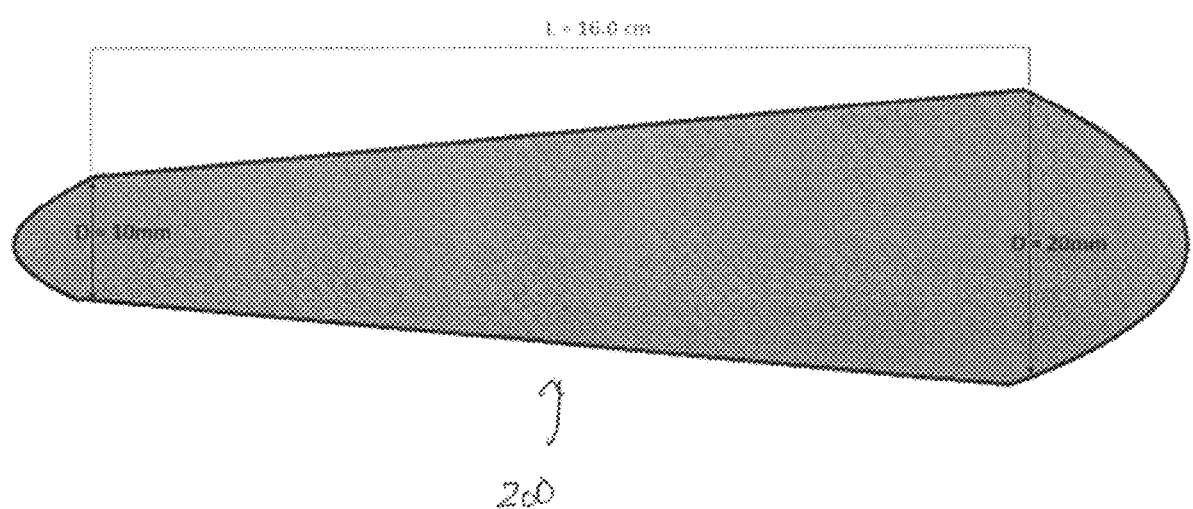
FIG. 7B shows a constant conductance flow balloon where a 16 cm portion of the balloon matches the constant conductance flow stent characteristics of the stent of FIG. 7A.
Figures 1, 2, 7C:
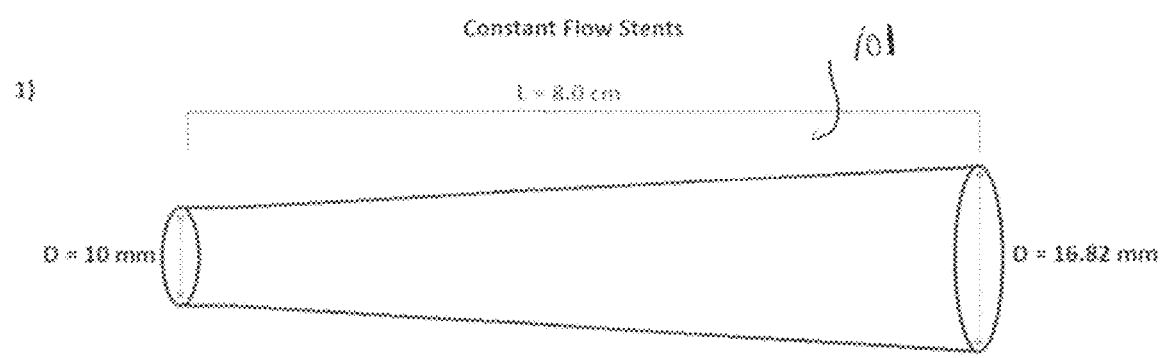
Figures 1, 2, 7D:
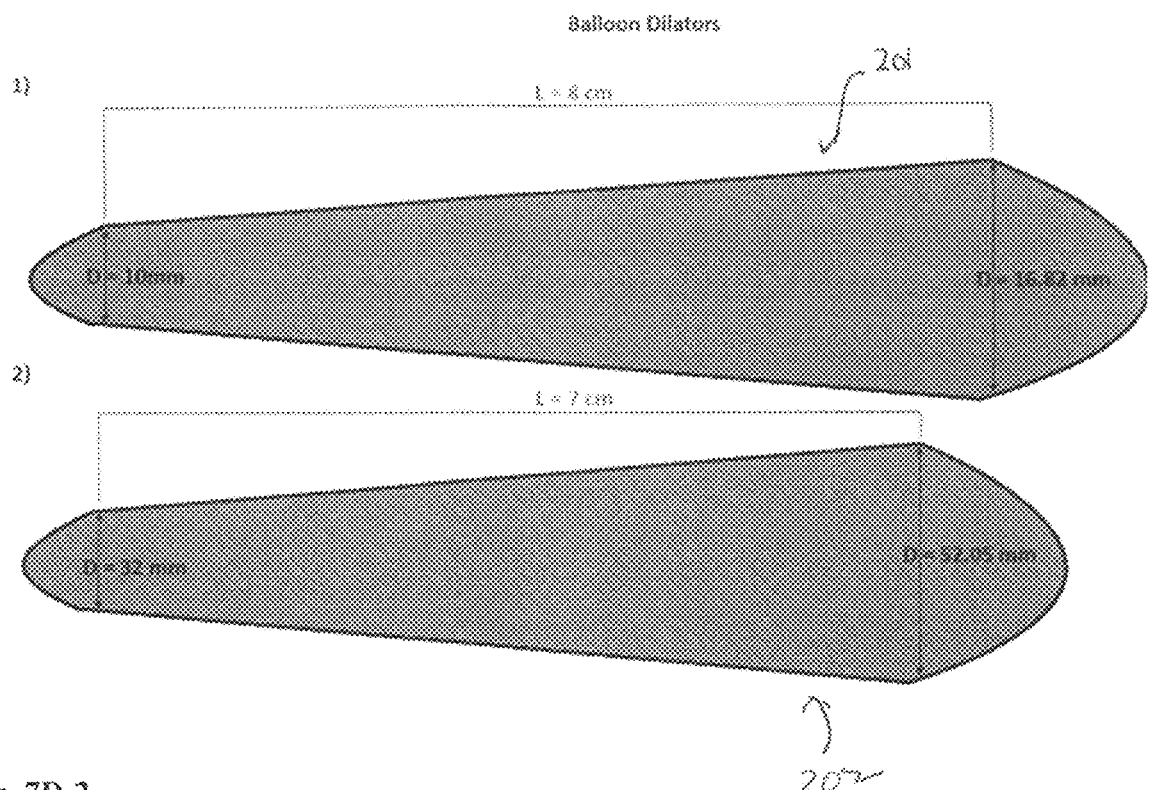

A conduit extending from the common femoral vein to the inferior vena cava was modeled in FIGS. 4A and 4B. It would have a continuously gradually increasing radius (r) to maintain the conductance constant. In FIGS. 4A and 4B, two lengths are depicted, 15 and 16 cm, each for two starting diameters at 10 mm (FIG. 4A) and 12 mm (FIG. 4B) respectively. FIG. 5 is a unitary or constant conductance diameter table for two starting diameters (10 and 12 mm), starting at station #0, the start of the conduit, and increasing in length at 1 cm intervals while progressively increasing in diameter after station 1 (i.e., a constant starting diameter of 1 cm), keeping $r^4/l$ constant=(starting diameter/2)$^4$/1. Additional tables with different starting diameters and lengths can be constructed using the calculation method described. FIGS. 6A-1 through 6A-5 are Excel spreadsheets showing dimensions for smaller sized conduit diameters (starting diameters 1, 2, 4, 8, 16, 32 mm) with stent ending radius depicted for "unitary" or constant conductance conduits for various lengths (for instance, 1 cm to 30 cm length). Similarly, FIG. 5A shows similar results for conduits starting at 1 cm diameter and the corresponding ending radius for various length conduits (1 to 20 cm). The concept is useful in constructing stents of various diameters and lengths that grow in diameter with length.

These tables can be used not only for designing "unitary" or constant conductance flow or increased flow stents but also for designing/constructing "unitary" balloons of the same diameter/length proportions, where balloon expansion is not uniform but expands non-uniformly, to approximate the unitary stent to be deployed, to match the balloon with the stent. To accomplish this, the balloon thickness can be varied, and/or the balloon materials can be varied with length. Alternatively, the balloon can be encased in a non-elastic unity shaped sleeve, so that when the balloon is expanded, it is restrained by the sleeve into the desired unitary form. Additionally, a non-uniform expanding balloon, such as a "unitary balloon" can be used for angioplasty without stenting, or for pre-dilatation of a stenosis before deploying a unitary or constant conductance stent 100 such as the stents 100, 101, 102 shown in FIGS. 7A and 7C-1 to 7C-2, and the corresponding balloons 200, 201 202 shown in FIGS. 7B and 7D-1 to 7D-2. The balloon of corresponding size can be used for deploying balloon expandable stents as well. Under dilatation and over dilatation of a unitary stent is possible by employing slightly smaller or larger balloons or sleeves chosen, using the tables shown, or as calculated.

Figure 8:
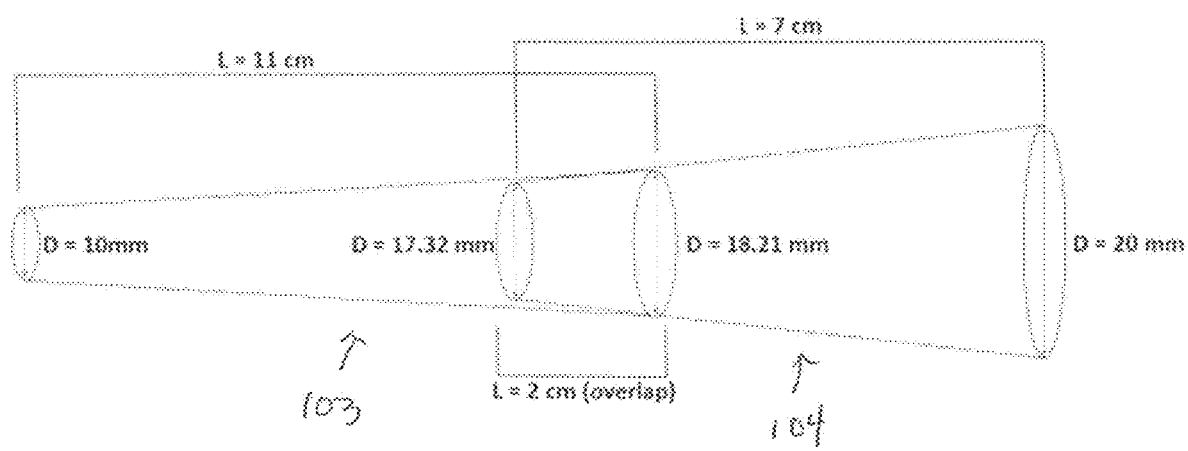
FIG. 8 is a perspective view of two stents to be inserted in line with a 2 cm overlap. The characteristics of these two stents are indicated.
Figure 9:
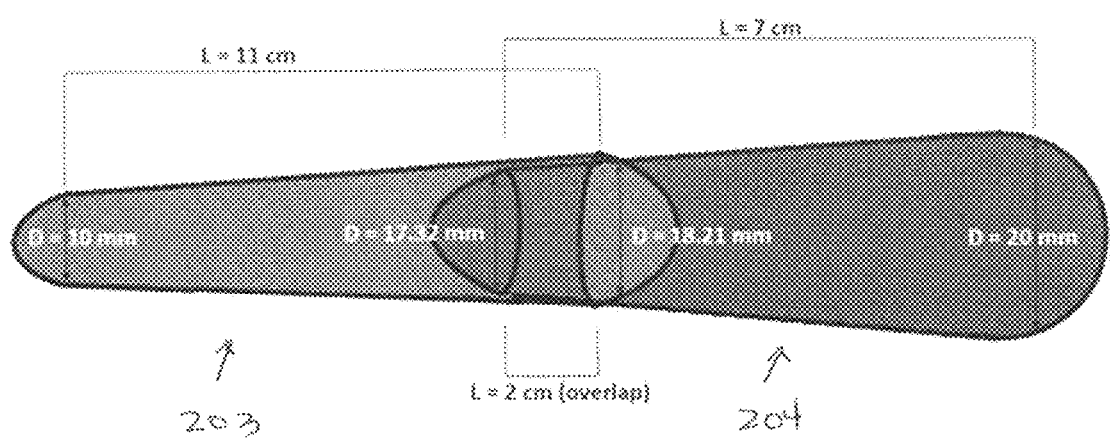
FIG. 9 shows a perspective view of two constant conductance flow balloons to be used with the constant conductance flow stents of FIG. 8. The intended overlap of the balloons when used in sequence is shown.
Figure 10:
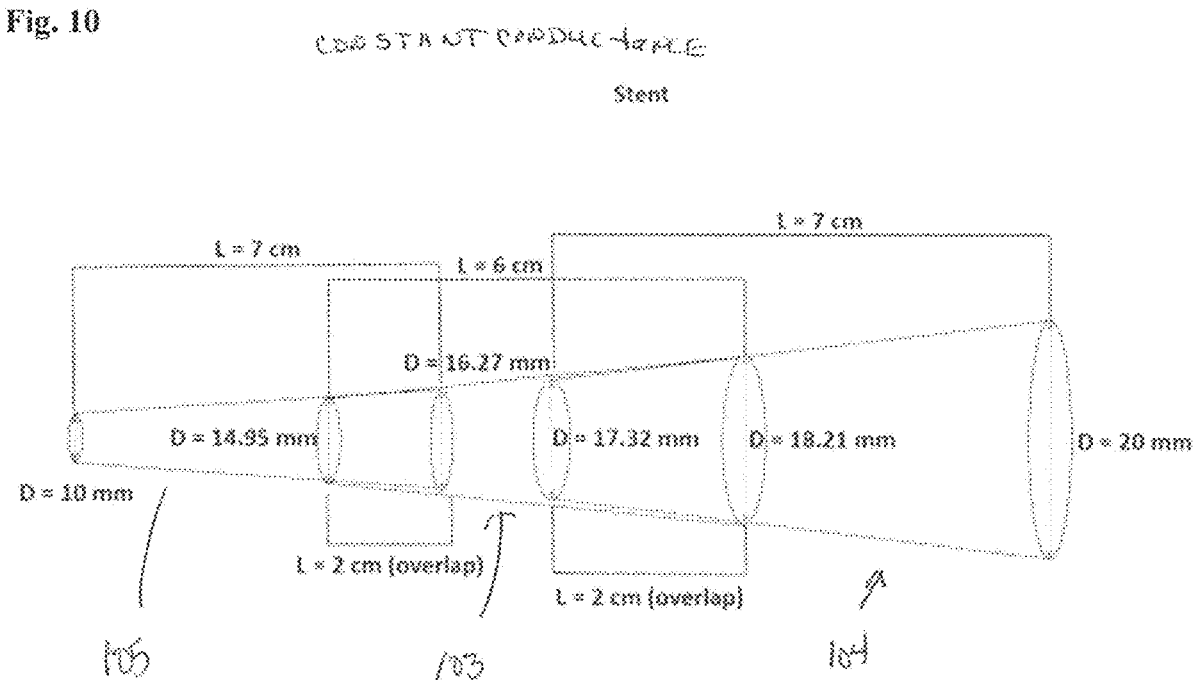
FIG. 10 is a perspective view of three stents to be inserted in line with a respective 2 cm overlap between adjacent stents. The characteristics of these three stents are indicated.
Figure 11:
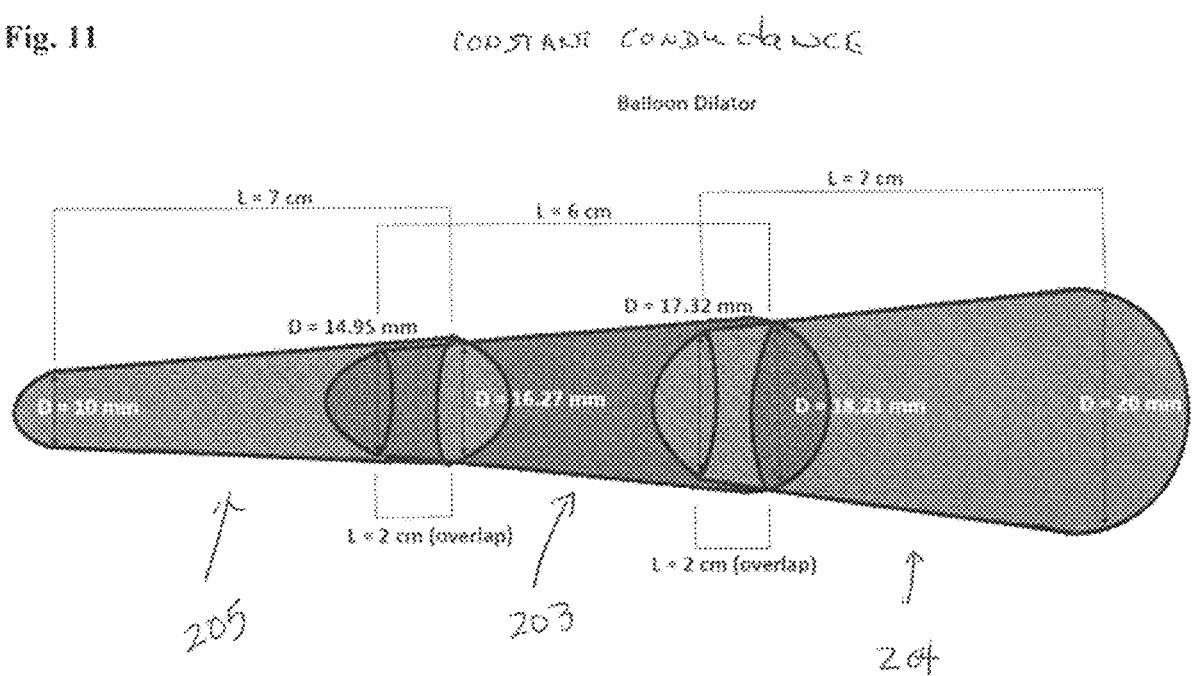
FIG. 11 shows a perspective view of three constant conductance flow balloons to be used with the constant conductance flow stents of FIG. 10. The intended overlap of the balloons when used in sequence is shown.

When shorter length balloons and stents are used, there should be some provision for overlap if the segment to be treated is longer than the length of a chosen balloon or stent. For instance, a 2.0 cm length stent overlap is shown in the FIGS. 8 and 10, with the corresponding balloons shown in FIGS. 9 and 11. Longer or shorter overlaps can be chosen according to the tables and spreadsheets. FIGS. 10 and 11 show a similar depiction for three overlapping stents 105, 103, 104 and overlapping balloons 205, 203, 204 with 2 cm of overlap at each overlapping position. For the overlapped stent, it would start of length Le−2 where Le is the ending length of the first stent. The initial stent would have a radius RI at this point that matches the first stent radius at Le−2. Hence the overlapped stent would have an initial radius of RI and expand at R4 from this point (assuming the initial stent was R4 growth to its end), where L in the second stent is measured from the start of the first stent (as the overlapped stents emulate a single long stent). The radius in the second stent expands so that $r^4/L=\text{constant}=(RI)^4/(Le-2)$ where L is measured for the start of the first stent. This provides for continuous R4 growth for stacked stents. Note, if a stent has a second expanding portion starting at length Le (measured from the stent start) with radius re, with growth factor RM, the constant in that portion will be $(re)^m/Le$.

The R4 geometric scaling factor can be illustrated in the following example: a parent vein receiving two tributaries, each 10 mm in diameter, will need to be only 12 mm in diameter (20% larger than each tributary) to maintain pressure unchanged even though the flow has doubled (FIG. 7). Zamir has calculated that doubling the radius of the conduit will reduce the energy needed to pump the same amount of fluid by 94% i.e., a mere 6% of the prior energy will do the same job. The venous system naturally grows as it gets closer to the heart.

Design and Use of Unitary or Constant Conductance Flow Stent Concept

The unitary or constant conductance flow stent concept is applicable in the venous system, and in some circumstances, the arterial system. The concept is to keep the conductance or flow constant in the stent, or portions of the stent, which can be achieved by maintaining the geometric factor ($r^4/L$) as a constant K in the growth portion of the stent. All examples used herein will have the stent grow after the first cm of length, with constant radius for that first cm, thus avoiding the ambiguity of examining $r^4/L$ as L→0.

As an example, consider a stent having a diameter of 18 mm (9 mm radius) (a common stent diameter used in the common iliac vein) at the end of a 1 cm length of constant radius, then $r^4/L=(1.8/2)^4/1=0.6561$, the constant K used for the remainder of this stent. Consequently, for a 2 cm long stent, the terminating radius would be $(0.6561*2)^{0.25}=1.070$ or a diameter of 2.14 mm. A 3 cm long stent would have a terminating radius of $(0.6561*3)^{0.25}=1.18$, or diameter of 2.36 mm; a 4 cm long stent would have radius of 12.7 mm, or a diameter of 25.4 mm; and for a stent length of 5 cm, the terminating radius would be 13.45 mm, or a diameter of 25.7 mm (an overall increase in cross-sectional area of about 123.3% (1.34/0.9)**2 (the iliac vein has been shown to tolerate as large as 24 mm diameter stent sizes).

As used, the "downstream" end of the constant conductance flow stent is larger. In the venous system, "downstream" is closer to the heart than the upstream end of the stent. This increase in diameter with length will assist to help offset flow reduction in the stent, to prevent stent malfunctions like in-stent restenosis caused by ingrowth of clot/tissue which accumulates and lines the wall of the stent. We have calculated the length necessary for various diameters in stents up to 5 cm length, in Table 2 for typical diameter stents used in the iliac system. The first cm in length is of constant diameter.

TABLE 2

| Stent length | 1 cm | 2 cm | 3 cm | 4 cm | 5 cm |
| --- | --- | --- | --- | --- | --- |
| CIV | 16 | 19 | 21 | 22.6 | 23.9 |
| EIV | 14 | 16.6 | 18.4 | 19.8 | 20.9 |
| CFV | 12 | 14.3 | 15.8 | 17 | 17.9 |

(stent diameter in mm)

As described, for a lengthwise cross section though a stent, the outer envelope preferably creases as a $4^{the}$ order polynomial, or $r^4$ with length. Such an increase is not required but is preferred. Slower growth and slower flows, achieved with $r^5/l$, $r^6/l$ or $r^7/l$ being constant with length can also provide benefits similar to constant conductance flow. Faster growth, and faster flow, such a linear growth, or growth by $x^2$ or $x^3$ or a combination such as a second order polynomial or a third order polynomial can also provide a benefit, as flow is further increased with R1, R2 or R3 growth, which can be useful in areas of the stent where restenosis or growth might accumulate from deposits with slower flow.

Stent Growth with Length

As long as the stent radius grows with length over portions of the stent (preferably consistent growth over each portion and preferably monotonic growth overall in the stent), such increased RN growth e.g., 1<n<4, or n>4, is considered "unitary like" growth or "near constant conductance flow herein, and within the scope of the invention. Flow as used herein is volumetric fluid velocity. Additionally, the stent's outer envelope may linearly increase between fixed stent radii at specific lengths, where those radii represent $r^4$ or RN growth at those radii/length combinations. Connecting the RN radii with linear radius therebetween approximates RN growth in piecewise steps. Such a stepwise construction is suitable for Z stents, such as the five Z stent 300, 301, 302, 303, 304 stacks shown in FIG. 12, as the Z stent diameter can be modified by changing the suture diameter at the top, middle or bottom of the Z stent, and is believed to make fabrication of a stepwise approximation to $r^4$ growth with Z stents (or other chosen growth factor) more efficient. Z stents and variations are described in U.S. Pat. Nos. 4,580,468; 5,282,824; 5,507,771 and 8,043,357 (all incorporated by reference herein). The ending radius of each stent segment Si, at length Li (measured from the start of the stent) is preferably unitary; that is ri is chosen so that $ri^4/Li$ a constant value at each starting and ending radius of each segment. If the length of augment Si is li, then the total length of the growth portion up to the radius in question Li will be $Li=\Sigma li$, where the sum stops at the respective radius of the segment in question. For a unitary or R4 approximation, $ri^4/Li$ is equal to the same constant, $ro^4/Lo$, where ro is the radius at the start of the first growth section of the stent, and Lo is preferably ($L_{eff}$) if the expansion section starts at the beginning of the stent, (L=0), or if the unitary growth section is near the beginning of the stent, then the preferred constant value will be $ri^4/(L_{eff}+LSO)$ where $L_{eff}$ is described above, and LSO is the length of the stent measured to the start of the unitary growth portion near the beginning of the stent or Lso is the initial length of the stent to the start of the growth section (For the examples herein, Lo is 1 cm and the radius is expressed in cm). While each starting and ending stent segment radius is unitary, the growth of the stent radius between may be either unitary or unitary like (near constant conductance growth) or linear. For instance, for the step segments in FIG. 12, each starting and ending segment radius is unitary, but the growth within each R4 segment radius is linear. The growth of each Z stent segment starting and ending radius can be unitary or other Rn growth (Rn or $r^n$ growth means $r^n/l$ is constant).

Rn growth over the entire stent or portions thereof, such as 1<n<4 or n>4, are considered to be "unitary-like" or "near constant conductance flow" stents. When $r^n/l$ is constant, n<4 implies faster radial growth and flow than R4 growth and R4 flow, and n>4, implies slower radial growth and slower flow than R4 growth. Each provides increased flow over the standard constant diameter stent. As used herein, flow is volumetric fluid velocity ($^m3/s$).

Radius growth with length is so that $r^n/l$ remain a constant, in all or a portion of the stent, where n>1, is within the scope of the invention. All segmented stents with segments or portions that are unitary or unitary-like growth, are within the scope of the invention. However, it is preferred that the growth of the stent in each segment or portion increases uniformly up to the ending segment radius. Stent growth overall is preferred to be monotonic growth but is not required.

An expanding or increasing dimeter stent is suitable for all stent types (braided, woven, laser cut mesh, and either self-expanding or balloon expandable) for the venous system. While a $4^{th}$ order polynomial increase is preferred for the outer envelope of all or portions of the stent (excluding for instance, constant diameter starting and possibly ending sections). These growth factors, e.g., $r^n/L$ where n<4 will grow faster than a constant conductance flow stent, and hence provide increasing flow rates, which can be a benefit in areas where deposits may accumulate, causing restenosis, Slower growth rates, e.g., where $r^n/L$ is constant, where n>4, such as n=5, 6, or 7 will be beneficial where long length stents or long stent stacks (e.g., multiple overlapping stents) are contemplated. While such growth is slower that $r^4$ growth and hence the volumetric flows is less than $r^4$ growth, the added benefit is that the ending radius size will be smaller than that in $r^4$ growth, and hence is more likely to be acceptable in a biological conduit system, such as a vein or artery. All such $r^n$ growth still provides increased flow over constant diameter stents.

For instance, fabrication of a stent with $r^4$ growth will yield a gradually expanding tube that will double its radius at 16 cm length. In many applications, this growth is too quick, resulting in an ending radius that is too large for the application. A more practical formulation is to keep $r^5/l$ or even $r^6/l$ or $r^7/l$ or larger, constant over the length of the stent or portions thereof. This will yield longer tube lengths before the radius doubles (Table 3); the conductive performance (volumetric flow) will be less than the constant $r^4/l$ formulation but still better (greater than) than that of a uniform cylinder. The ending diameters for various lengths with initial diameters of, 6, 8, and 10 mm is shown in Table 4.

TABLE 3

Conduit radius increase with length

| Variable Constant | Length at which $R_{initial}$ doubles (cm) |
|---|---|
| $\frac{r^2}{L}$ | 4 |
| $\frac{r^3}{L}$ | 8 |
| $\frac{r^4}{L}$ | 16 |
| $\frac{r^5}{L}$ | 32 |
| $\frac{r^6}{L}$ | 64 |

TABLE 4

Initial and end diameter of uniform cylindrical and test conduits

| Constant Geometric Factor | Initial Diameter (mm) | Ending Diameter at L = 160 mm (mm) | Ending Diameter at L = 310 mm (mm) | Ending Diameter at L = 620 mm (mm) |
|---|---|---|---|---|
| r | 4 | 4.00 | 4.00 | 4.00 |
|  | 6 | 6.00 | 6.00 | 6.00 |
|  | 8 | 8.00 | 8.00 | 8.00 |
|  | 10 | 10.00 | 10.00 | 10.00 |
| $\frac{r^4}{L}$ | 4 | 8.00 | 9.44 | 11.22 |
|  | 6 | 12.00 | 14.16 | 16.84 |
|  | 8 | 16.00 | 18.88 | 22.45 |
|  | 10 | 20.00 | 23.60 | 28.10 |
| $\frac{r^5}{L}$ | 4 | 6.96 | 7.95 | 9.13 |
|  | 6 | 10.45 | 11.92 | 13.70 |
|  | 8 | 13.93 | 15.90 | 18.26 |
|  | 10 | 17.41 | 19.87 | 22.83 |
| $\frac{r^6}{L}$ | 4 | 6.35 | 7.09 | 7.96 |
|  | 6 | 9.52 | 10.63 | 11.94 |
|  | 8 | 12.70 | 14.18 | 15.92 |
|  | 10 | 15.87 | 17.72 | 19.89 |

To demonstrate performance of slower growth stents, the following experiment was done:

Fabrication of Experimental Conduits

To test less aggressive growth stent designs, $r^n$ growth conduits with n>4 were designed using engineering software (Autodesk, Inc.; San Rafael, CA) and fabricated in a commercial 3D printer (Stratasys; Eden Prairie, MN).

Experimental Test Model

Figure 13:
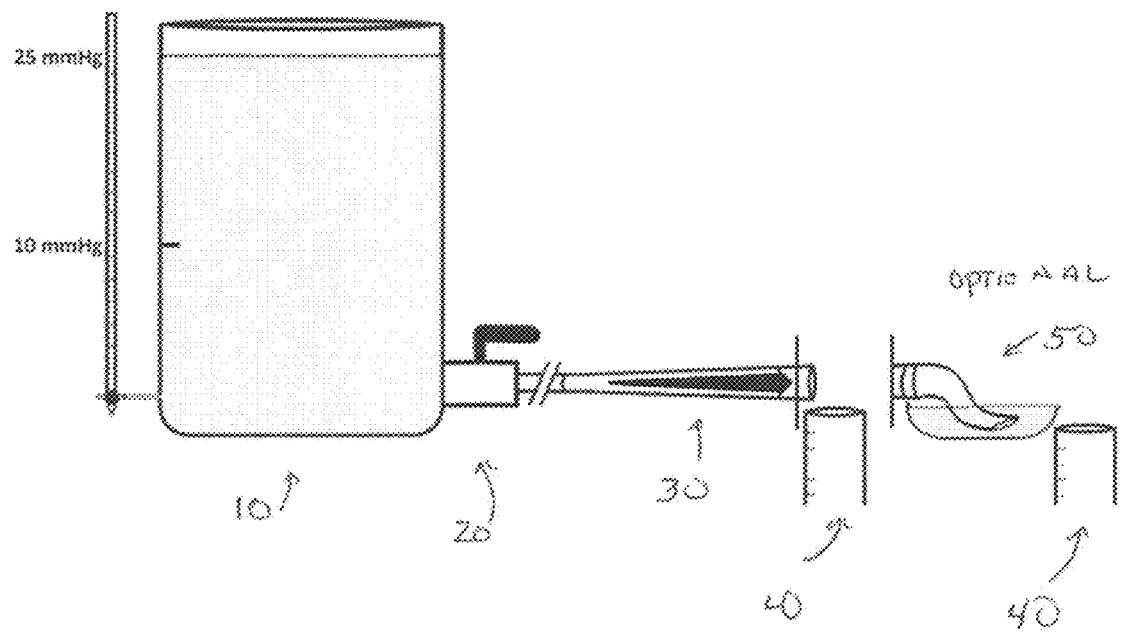
FIG. 13 is an illustration of a side view of one experimental system used to test the output of an expanding conduit.
Figure 14A:
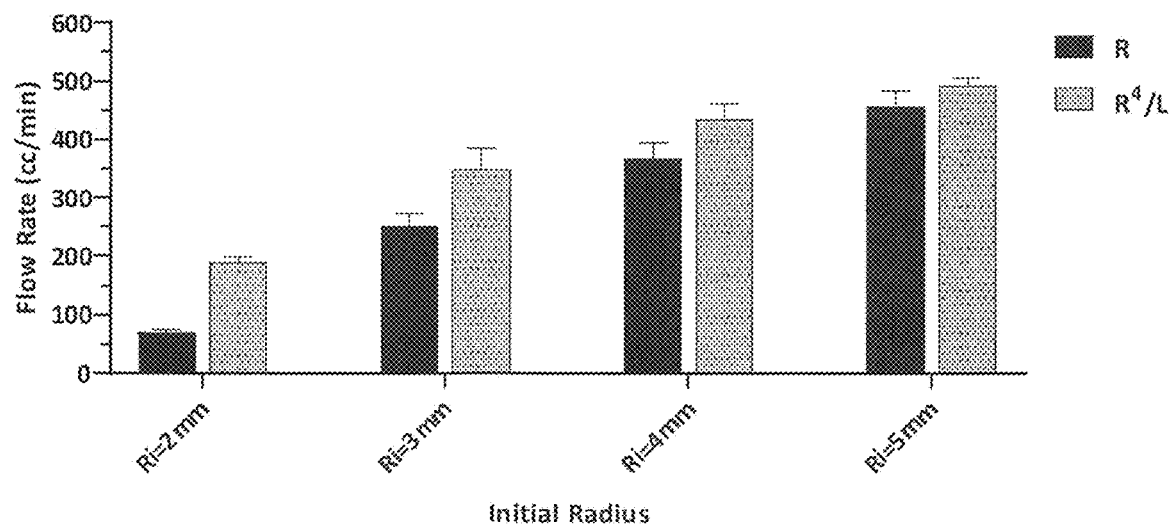
FIG. 14A is a set of bar graphs comparing flow rates of constant radius flow versus constant conductance flow through grafts of various diameters and length 160 mm where the initial pressure was 10 mmHg in the experimental setup of FIG. 13.
Figure 14B:
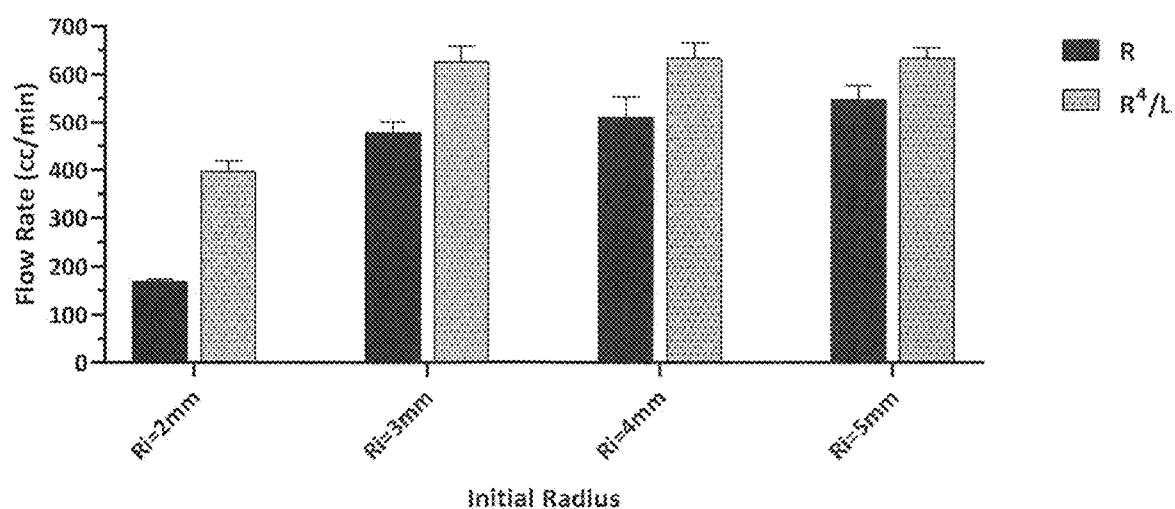
FIG. 14B is a set of bar graphs comparing flow rates of constant radius flow versus constant conductance flow through grafts of various diameters and length 160 mm where the initial pressure was 25 mmHg in experimental setup of FIG. 13.

The basic flow model consisted is of a header tank 10 with outflow controlled by a calibrated ball valve 20 (FIG. 13). The ball valve was kept open at the same setting for all flows. The various conduits 30 tested were connected to the ball valve. Each conduit had an initial starting length li; here, 1 cm, wherein the radius was constant. It is believed that the constant starting radius allows flow from the pressurized system to stabilize before entering the expanding section. It also avoids the potential ambiguity of evaluating $r^n/l$ as l→0. Conduit outflow was open to the atmosphere (open system) and was allowed to drain into a graduated cylinder 40 for timed measurement (cc/minute). In some experiments, a partially closed system of drainage was used: the conduits were connected to a short Penrose drain 50 (Diameter=3.5 cm; Length=13 cm) discharging under the fluid level in a shallow pan before emptying into the output cylinder (option, FIG. 13). The system prevented air from entering the conduit at the discharge end, functioning similar to the Heimlich valve. The tank system was filled with a 2:3 mixture of glycerol and water with a viscosity of 0.04 poise. Each flow measurement is an average of 5 runs. As shown in the bar graphs of FIGS. 14A and 14B, 15A and 15B, the flow rate of a constant diameter conduit is always less than the expanding conduits, for all length tested (1.6 cm, 3.1 cm and 6.2 cm) and for all starting radii tested of 2 mm, 3 mm 4 mm, and 5 mm. As expected, flow rates with $r=K*(\sqrt[4]{l})$ was greater than flows with $r=K*(\sqrt[5]{l})$ which flows were greater than flows with $r=K*(\sqrt[6]{l})$, for two different starting pressures (FIGS. 14A and 14B).

Results

Figure 15A:
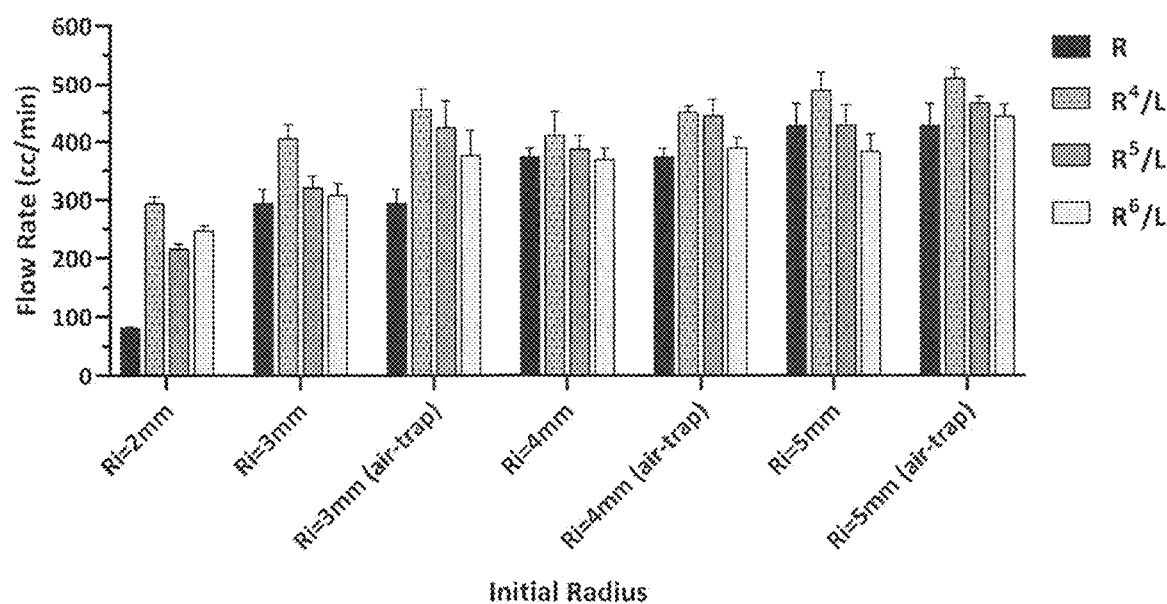
FIG. 15A is a set of bar graphs comparing flow of constant radius flow versus $R^4/L$, $R^5/L$ and $R^6/L$ flow through grafts of various diameters and length of 310 mm with and without an air trap where the initial pressure was 10 mmHg in the setup of FIG. 13.
Figure 15B:
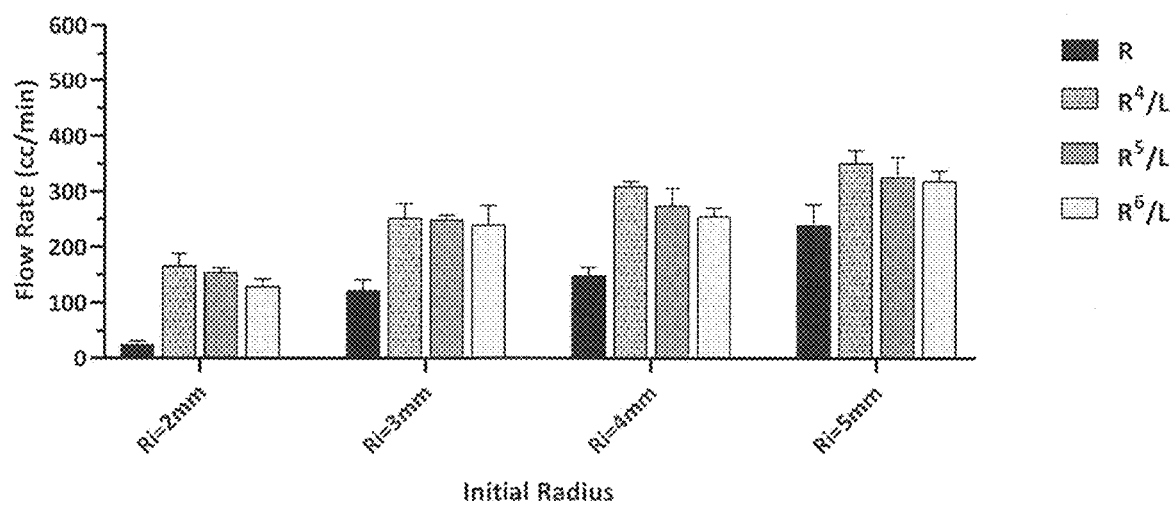
FIG. 15B is a set of bar graphs comparing flow of constant radius flow versus $R^4/L$, $R^5/L$ and $R^6/L$ flow through grafts of various diameters and length of 620 mm where the initial pressure was 10 mmHg in the setup of FIG. 13.

The flow rates of expanding caliber conduits ($r^{4-6}$) compared to traditional constant radius cylindrical conduits are shown in Table 5 and FIGS. 15A and 15B. The expanding caliber stents yields a significantly improved flow from 14% to 563% in all but a few instances. In the latter instances, the outflow stream was observed to be separated from part of the tube outlet circumference, suggesting flow separation from the wall; i.e., the flow was no longer laminar for some length near the outflow end. This problem was substantially reduced when the Penrose air-trap was used (Table 6). The air trap restricts the flow of air into the conduit at the discharge end, more closely emulating a closed fluid flow system, like the arterial or venous systems. Flow separation/cavitation should not be an issue in closed biological flows. In closed flows where the fluid completely fills the conduit and the flow is driven by a pressure gradient, the incidence of transition to non-laminar flow should be reduced, in an expanding conduit, as in an expanding conduit, where $r''/l$ is constant, the fluid velocity still declines with length.

TABLE 5

Mean conduit flow rate when R, $R^4/L$, $R^5/L$, and $R^6/L$ are held constant (no air-trap)

| Conduit Length (mm) | Initial Radius (mm) | Constant Radius Flow (cc/min) | Constant $R^4/L$ Flow (cc/min) (% improvement) | Constant $R^5/L$ Flow (cc/min) (% improvement) | Constant $R^6/L$ Flow (cc/min) (% improvement) |
|---|---|---|---|---|---|
| Input Pressure = 10 mmHg ||||||
| 160 | 2 | 71 | 188 (+165%***) | — | — |
|  | 3 | 251 | 349 (+39%***) | — | — |
|  | 4 | 368 | 435 (+18%**) | — | — |
|  | 5 | 458 | 492 (+7%) | — | — |
| 310 | 2 | 81 | 294 (+263%***) | 216 (+167%***) | 247 (+205%***) |
|  | 3 | 294 | 406 (+38%***) | 321 (+9%) | 308 (+5%) |
|  | 4 | 373 | 411 (+10%) | 387 (+4%) | 369 (−1%) |
|  | 5 | 428 | 489 (+14%*) | 428 (0%) | 383 (−11%) |
| 620 | 2 | 26 | 166 (+538%***) | 154 (+492%***) | 129 (+396%***) |
|  | 3 | 122 | 253 (+107%***) | 249 (+104%***) | 240 (+97%***) |
|  | 4 | 149 | 310 (+108%***) | 275 (+85%***) | 256 (+72%***) |
|  | 5 | 240 | 352 (+47%***) | 327 (+36%**) | 320 (+33%**) |
| Input Pressure = 25 mmHg ||||||
| 160 | 2 | 169 | 398 (+136%***) | — | — |
|  | 3 | 478 | 628 (+31%***) | — | — |
|  | 4 | 513 | 636 (+24%***) | — | — |
|  | 5 | 550 | 637 (+16%***) | — | — |
| 310 | 2 | 157 | 427 (+172%***) | 301 (+92%***) | 285 (+82%***) |
|  | 3 | 401 | 512 (+28%***) | 377 (−6%) | 386 (−4%) |
|  | 4 | 475 | 575 (+21%***) | 447 (−6%) | 487 (+3%) |
|  | 5 | 549 | 662 (+21%) | 491 (−11%*) | 520 (−5%) |
| 620 | 2 | 68 | 451 (+563%***) | 364 (+435%***) | 301 (+343%***) |
|  | 3 | 267 | 520 (+95%***) | 476 (+78%***) | 433 (+62%***) |
|  | 4 | 403 | 551 (+37%***) | 504 (+25%***) | 509 (+26%***) |
|  | 5 | 503 | 632 (+26%**) | 592 (+18%***) | 522 (+4%) |

*P < 0.05 vs. constant radius flow
**P < 0.01 vs. constant radius flow
***P < 0.001 vs. constant radius flow

TABLE 6

Mean conduit flow rate with and without Penrose air-trap (conduit length = 310 mm)

| Initial Radius (mm) | Constant R Flow$^a$ (cc/min) | Constant $R^4/L$ Flow (cc/min, %) | Constant $R^4/L$ + air-trap Flow (cc/min, %) | Constant $R^5/L$ Flow (cc/min, %) | Constant $R^5/L$ + air-trap Flow (cc/min, %) | Constant $R^6/L$ Flow (cc/min, %) | Constant $R^6/L$ + air-trap Flow (cc/min, %) |
|---|---|---|---|---|---|---|---|
| Input Pressure = 10 mmHg ||||||||
| 3 | 294 | 406 (+38%***) | 456 (+55%***) | 321 (+9%) | 424 (+44%***) | 308 (+5%) | 376 28%**) |
| 4 | 373 | 411 (+10%) | 450 (+21%***) | 387 (+4%) | 444 (+19%***) | 369 (−1%) | 389 (+4%) |
| 5 | 428 | 489 (+14%*) | 500 (+17%*) | 428 (0%) | 467 (+9%*) | 383 (−11%) | 443 (+4%) |

TABLE 6-continued

Mean conduit flow rate with and without Penrose air-trap (conduit length = 310 mm)

| Initial Radius (mm) | Constant R Flow[a] (cc/min) | Constant $R^4/L$ Flow (cc/min, %) | Constant $R^4/L$ + air-trap Flow (cc/min, %) | Constant $R^5/L$ Flow (cc/min, %) | Constant $R^5/L$ + air-trap Flow (cc/min, %) | Constant $R^6/L$ Flow (cc/min, %) | Constant $R^6/L$ + air-trap Flow (cc/min, %) |
|---|---|---|---|---|---|---|---|
| Input Pressure = 25 mmHg | | | | | | | |
| 3 | 401 | 512 (+28%***) | 570 (+42%***) | 377 (−6%) | 553 (+38%***) | 386 (−4%) | 449 (+12%*) |
| 4 | 475 | 575 (+21%***) | 602 (+27%**) | 447 (−6%) | 566 (+19%**) | 487 (+3%) | 505 (+6%) |
| 5 | 549 | 662 (+21%**) | 638 (+16%**) | 491 (−11%*) | 602 (+10%**) | 520 (−5%) | 553 (+1%) |

*P < 0.05 vs. constant radius flow
**P < 0.01 vs. constant radius flow
***P < 0.001 vs. constant radius flow
[a]Flow separation did not occur in the constant radius conduits; Penrose air-traps did not affect these flows.

Discussion

Accretive manufacturing (3-D printing) makes it much easier to fabricate expanding caliber stents for biological use. 3D printing with Nitinol is possible for stents, but traditional stent manufacturing techniques could also be used for these expanding stents.

There is a practical limit to the length of the stent depending upon location and use. Examination of Table 3 (length of conduit when initial radius doubles) and Table 5 (measured flow rated for the conduits tested without an air trap) suggests that up to ≈16 cm is practical for stent designs keeping $r^4/L$ constant. As shown in Table 7, for common iliac vein stents of 14 mm diameter, the ending radius is calculated for various length conduits for different $r^N$ N=4, 5, or 6. with all conduits having an initial starting length (1 cm) of constant radius. As shown, combinations up to 64 cm length appear practical for stents keeping $r^5/L$ constant. Longer lengths may be required for particular applications and are possible keeping $r^6/L$ or $r^7/L$ or higher r values constant. Fabrication techniques described above or known to those of ordinary skill in the art may be used to construct the rN expanding sent/conduit.

TABLE 7

Expanding stent caliber configuration for Iliac vein (Initial Diameter = 14 mm)

| Length (cm) | Constant $R^4/L$ Radius (mm) | Constant $R^5/L$ Radius (mm) | Constant $R^6/L$ Radius (mm) |
|---|---|---|---|
| 0 | 14.00 | 14.00 | 14.00 |
| 1 | 14.00 | 14.00 | 14.00 |
| 2 | 16.65 | 16.08 | 15.71 |
| 3 | 18.43 | 17.44 | 16.81 |
| 4 | 19.80 | 18.47 | 17.64 |
| 5 | 20.93 | 19.32 | 18.31 |
| 6 | 21.91 | 20.03 | 18.87 |
| 7 | 22.77 | 20.66 | 19.36 |
| 8 | 23.55 | 21.22 | 19.80 |
| 9 | 24.25 | 21.73 | 20.19 |
| 10 | 24.90 | 22.19 | 20.55 |
| 11 | 25.50 | 22.62 | 20.88 |
| 12 | 26.06 | 23.01 | 21.18 |
| 13 | 26.58 | 23.38 | 21.47 |
| 14 | 27.08 | 23.73 | 21.73 |
| 15 | 27.55 | 24.06 | 21.99 |

The expanding caliber stents may have an advantage over the traditional cylindrical prosthetics in the following areas of vascular surgery.

Venous Stents

Venous caliber naturally scales up as tributaries coalesce. The iliac veins are the most common site for stent placement. Common femoral vein is 12 mm in diameter. The external iliac vein is ≈14 mm in diameter; the common iliac vein is slightly larger at ≈16 mm diameter. A gradual configuration as shown in Table 7 starting at 14 mm diameter may provide greater flow than current cylindrical designs. In-stent restenosis is a substantial problem in iliac vein stents and correlates with low inflow. It is believed that the expanding stent will ameliorate these problems of legacy design. The most frequent cause of stent thrombosis is poor inflow; outflow problems are less frequent causes. In either case, the pressure gradient ($\Delta P$) is reduced causing flow decrease. A greater flow rate may be possible with the reduced gradient if the expanded configuration stent is used. Hence, a stent stack can be designed starting at 12 cm diameter in the common femoral, growing at RN until it reaches 14 mm diameter at the external iliac, then growing at RM until it reaches 16 mm diameter at the common iliac and then growing, for instance, at R4 to the end of the stack. Her N and M can be solved for given the respective lengths in each vein segment to be stented. Alternatively, a single RN growth can be chosen, to best fit the circumstances.

Sleeved Stents

These composite stent/sleeved or grafts are used in specific anatomic locations where the prosthetic is subject to external compression/stress. Flow characteristics of the expanded configuration may function better where both the stent and graft (a non-elastic sleeve on the exterior of the sent) expands equally. Indeed, the stent expansion may be greater, but the sleeve will control/limit the expansion of the stent.

As will be understood by one of skill in the art, the length l used in ($r=k^n\sqrt{l}$), is measured from the start of the conduit, not the start of the expanding section) for standalone stents. Long "stents" can be constructed in steps or segments, by overlapping adjacent stents (such as 2 cm) to create longer stent stacks that emulates a single long stent. Overlapping stent diameters preferably match, by choosing the overlapped segment starting diameters to match, and selecting the geometric expansion of growth factor to match. However, as the stack of stents is used to emulate a single stent, the length used in RN growth is measured from the beginning of the first stent in the stack.

Stents ($r=K^n\sqrt{l}$ where n≥4) can have endless applications where the flow rate through the application is an important factor to the functioning of the system, including the arterial system. Stents are also used to correct intimal hyperplasia at the venous end of dialysis grafts and fistulas. An expanding caliber stent may function better in these locations. In biological systems, use of expanding radii stents should greatly reduce restenosis in these stents.

Stent Designs

In one embodiment, for a stent of selected length L1, the upstream and downstream terminating diameters are chosen (for instance, the upstream diameter can be selected as the standard or minimal diameter for the particular vein segment and choosing the downstream diameter to match the desired geometric factor constant, e.g., $r^4/l$, or $r^n/l$ for n<4 for faster growth and flows, or $r^n/l$ for n.4 for slower growth and slower flow rates then a constant conductance flow design. Alternatively, the starting and ending diameters can be chosen and then solve for the best fitting value of n in $r^n/l$, over the selected length L1. Note that n does not have to be an integer value, and n can represent at polynomial of the chosen degree e.g., $4^{th}$ order, $5^{th}$ order polynomial, etc.

The stents described are for a vein or artery segment that is substantially uniform in diameter absent a stenosis. If the vein or artery segment to be stented, normally has a natural increase in size, that natural increase may be accounted for in the designed "unitary" or increased flow stent, or near constant conductance flow stents, for instance, by increasing the selected stent terminating diameter by adding an additional amount equal to the natural increase in vein size, to get a "unitary plus" sized stent, by selecting the best RN growth to get the chosen diameter.

Stents up to 15 cm long are being produced using constant diameter stents in standard dimensions. These current stents are usually of fixed unchanging diameter. However, there are stents manufactured as expanding tapered stents, See U.S. Pat. Nos. 9,655,710; 8,623,070; 7,637,939, typically chosen to fit an expanding biological conduit. The unitary or constant conductance flow stent concept can be used even in long stents, such as 15 or even 20 cm in length, such as for use in the iliac vein. Such long stents may jail the hypogastric vein, which is well tolerated. However, for long stents, the elasticity of the vein wall can be a limiting factor, and a growth factor for slower growth than the $4^{th}$ power for the radius per cm length may be more practical and desirable, such as $5^{th}$, $6^{th}$ or $7^{th}$ power in r.

Additionally, the invention includes stents that have a portion that is increased volumetric flow such as constant conductance or near constant conductance flow. Consider a stent that has an initial radius r1 of 15 mm or 1.5 cm) and remains constant for two cm. For the next 5 cm, the stent is unitary, with the starting radius of 1.5 cm. In other words, for the next 5 cm, $r^4/L$ remains constant, where L is the distance from the starting point of the stent to the expanding section start, and at the $7^{th}$ cm of the stent, L=7 cm). at the end of the growth portion. the stent may continue with a fixed radius or alternatively, the radius in the final portion may further increase with a different RN factor or remain constant or even decrease (not preferred). For instance, at the end of the unitary portion described above, the stent may continue for another 2 cm but over that 2 cm, the radius may smoothly decline, such as linearly (e.g., a first order polynomial), to end at the normal radius of the resident vein, and thus allow for a smooth flow transition from the end of the unitary portion to the end of the stent back into the vein. One design factor is to have the end of the stent designed so that the flow at the end is at least as large as that in terminating vein location.

Slower growth rates than a constant conductance flow stent (e.g., $r^n/l$ is constant) but where n>4, can be used in long stents with lesser impact on vein walls but still providing the benefit of greater flows then provided by a constant diameter stent. Note the growth exponent n does not have to be an integer and can be a polynomial.

The stents and balloons described herein may include radio markers to allow the balloons or stents to be visualized during placement for proper positioning.

The invention includes unitary or constant conductance balloons or near constant conductance balloons, where the radius of the balloon expands with length to match the growth of the stent. For instance, by varying balloon materials or by use of a balloon sleeve that assumes the desired expanded shape. If the stent is a piece-wise growth described above, the balloon should match the growth. The balloon can be constructed of differing materials to provide such varying expansion, or the balloon can also be sleeved to control its growth into the desired shape, by having the sleeve take on the desired expanded shape.

As described, the unitary or near unitary stent can be designed to fit the vein or arterial restrictions and provide increased flows. The stents are preferable to monotonic growth, but there are instances where the growth can decrease. For instance, if a stent bifurcates into two, the two stents will have smaller diameters than the parent, and the bifurcated stents can grow with constant or near constant conductance flow; in these instances, the length in the bifurcated stent can start at the bifurcation.

Measurement of L in a Growth Section

As described, it is preferred that in a growth section where $R^N/L$ is constant, that L is measured from the beginning of the stent system. If you measure the length from the start of the growth stent, then the growth in this case is not identical to that when length is measured from the start of the system. This occurs because $r=\sqrt[n]{(Kl)}$ in the growth section. The radius is smaller in a growth section when L is measured from the start of the stent system. Note also that the growth constant K is a different value in the two systems, as $K=(rs)^n/Ls$, where rs is the radius at the start of the growth section, and Ls is the stent length at the start of the growth section.

As an example, consider a two stent system, each 10 cm length, with a 1 cm overlap, where the first conduit is constant, radius of 2 cm, the second conduit grows at R4 after the 1 cm overlap.

L=0 at beginning of system L=0 at start of growth conduit
$K=2^4/10=1.6$ $K=2^4/1=16$
length at end of second stent=19 length at end of second stent=10
(radius at L=19)=$\sqrt[4]{KL}=\sqrt[4]{1.6*19}$=2.34 (radius at L=10))=$\sqrt[4]{KL}=\sqrt[4]{16*10}$=3.55

Clearly, the two measurements of L result in a different growth profile. Measuring L in a growth section from the start of the stent in a growth section is more manufacturer friendly. Otherwise, the manufacturer will have to custom build each stent, with an understanding of the length of the stent system prior to the stent in question. Measuring L from the start of the stent system more closely emulates a single stent particularly in performance.

You can build a stent system using growth stents sections where the growth is referenced from the start of the growth stent. Such a stent system will have different growth profile and different performance characteristics than one where length L is measured from the system start. Care should be taken understanding length measurement which system was used.

The invention claimed is:

1. An expandable stent of length L comprising a structure having a tubular shape when expanded, where the expanded shape includes a radius r at each length l of the stent, such that when expanded, the stent has a portion where the radius r at each length l of the stent in the portion grows with l such that $r^n/l$ is a constant at each l in the portion, where n=4, or where the growth of the radius r with length l in the portion is less that that where $r^4/l$ is a constant in the portion, where l is measured from a beginning end of the stent, and where the length at the beginning of the stent is either 0 or a nonzero value c.

2. The expandable stent of claim 1 where the portion terminates at an end of the stent.

3. The expandable stent of claim 1 where the portion begins after the beginning end of the stent and ends before a termination end of the stent.

4. The expandable stent of claim 1 where the stent is configured to be self-expanding.

5. The expandable stent of claim 1 where the stent is configured to be balloon expandable.

6. The expandable stent of claim 1 wherein n is a polynomial of degree 4, such that the growth of the stent radius with length in the portion is monotonic.

7. The expandable stent of claim 1 having an initial portion at a beginning of the stent, where r is constant over the initial portion.

8. The expandable stent of claim 1 having a terminating portion beginning after a termination of the portion and ending at the terminating end of the stent where r is constant over the terminating portion.

9. An expandable stent of length L comprising a structure having a tubular shape when expanded, where the expanded shape includes a radius r at each length l of the stent, such that when expanded, the stent has a portion where the radius grows with stent length l in the portion so that the growth of r is constant conductance growth in the portion, or near constant conductance growth in the portion.

10. The expandable stent of claim 1 where the portion begins at the beginning end of the stent and the length l at the beginning end of the stent is set to a pre-determined effective length.

11. The expandable stent of claim 1, where the growth of the radius r with length l in the portion, which is less that that where $r^4/l$ is a constant, includes growth of r with l in the portion such that $r^n/l$ is constant, where n>4.

12. The expandable stent of claim 10, where the predetermined effective length is $L_{eff}$.

13. The expandable stent of claim 1 where the length l is defined as, ml+C, where C is a constant and ml is a measured length measured from the beginning end of the stent, where ml=0.

* * * * *